United States Patent [19]

Weber et al.

[11] Patent Number: 5,976,836
[45] Date of Patent: Nov. 2, 1999

[54] METHODS AND COMPOSITIONS FOR ENHANCING ERYTHROMYCIN PRODUCTION

[75] Inventors: J. Mark Weber, Chicago; Paul E. Hessler, Lake Bluff; Peter E. Larsen, Downers Grove; Minh B. Luu, Chicago, all of Ill.

[73] Assignee: FermaLogic, Inc., Chicago, Ill.

[21] Appl. No.: 08/852,401

[22] Filed: May 7, 1997

[51] Int. Cl.$^6$ .............................. C12P 21/06; C12N 9/24; C12N 1/20; C07H 21/04
[52] U.S. Cl. ............... 435/69.1; 435/200; 435/257.3; 435/252.33; 435/252.35; 536/23.1; 536/23.2; 536/23.7
[58] Field of Search .................... 435/69.1, 200, 435/252.3, 252.33, 252.35; 536/23.1, 23.2, 23.7

[56] References Cited

U.S. PATENT DOCUMENTS

| | | | |
|---|---|---|---|
| 2,653,899 | 9/1953 | Bunch et al. | 167/65 |
| 5,141,926 | 8/1992 | Weber et al. | 514/29 |
| 5,462,862 | 10/1995 | Groenen et al. | 435/69.1 |
| 5,514,544 | 5/1996 | Rao et al. | 435/6 |
| 5,563,064 | 10/1996 | Hutchinson et al. | 435/252.3 |

OTHER PUBLICATIONS

Bussy, L.B., et al., *J. Bacteriol.*, 175:6348–6353, (1993).
Chater, K.F. et al., *Biotechnology 6*: Washington, Germany, (1997).
Fernandez, Moreno, M.A., *J. Bacteriol*, 174:2958–2967, (1992).
Geistlich, M., et al.., *Mol. Microbiol*, 6:2019–2029 (1992).
Horinouchi, S., et al., *J. Bacteriol.*, 155:1238–1248, (1983).
Horinouchi, S., et al., *Agric. Biol. Chem.*, 48:2131–2133, (1984).
Ishizuka, H., et al., *J. Bacteriol.*, 174:7585–7594, (1992).
Quenner, S.W., et al., *American Society for Microbiology*, Washington, D.C. 155–169, (1986).
Romero, N.M., et al., *Nucleic Acids Res.*, 29:2767–2772, (1992).
van Wezel, G.P., et al., *Mol. Microbiol* 23:537–549 (1997).
Ward, J.M. et al., *Mol. Gen. Genet.*, 203:468–478 (1986).
Weber, J.M. et al., *J. Bacteriol.*, 172:2372–2383, (1990).
Weber, J.M. et al., *Gene*, 75:235–241, (1989).
Weber, J.M. et al., *J. Bacteriol.*, 164:425–433, (1985).
Weber, J.M. et al., *Gene.*, 68:173–180, (1988).
Weicker, M.J. et al., *J. Biol. Chem.*, 267:15869–15874, (1992).

*Primary Examiner*—Karen Cochrane Carlson
*Assistant Examiner*—Nashaat T. Nasheed
*Attorney, Agent, or Firm*—Rockey, Milnamow & Katz, LTD

[57] ABSTRACT

The present invention provides isolated and purified polypeptides that increase antibiotic production, polynucleotides that encode those polypeptides, expression vectors containing those polynucleotides, host cells transformed with those expression vectors, a process of making the polypeptides using those polynucleotides and vectors, and processes using those polypeptides and polynucleotides.

19 Claims, 13 Drawing Sheets

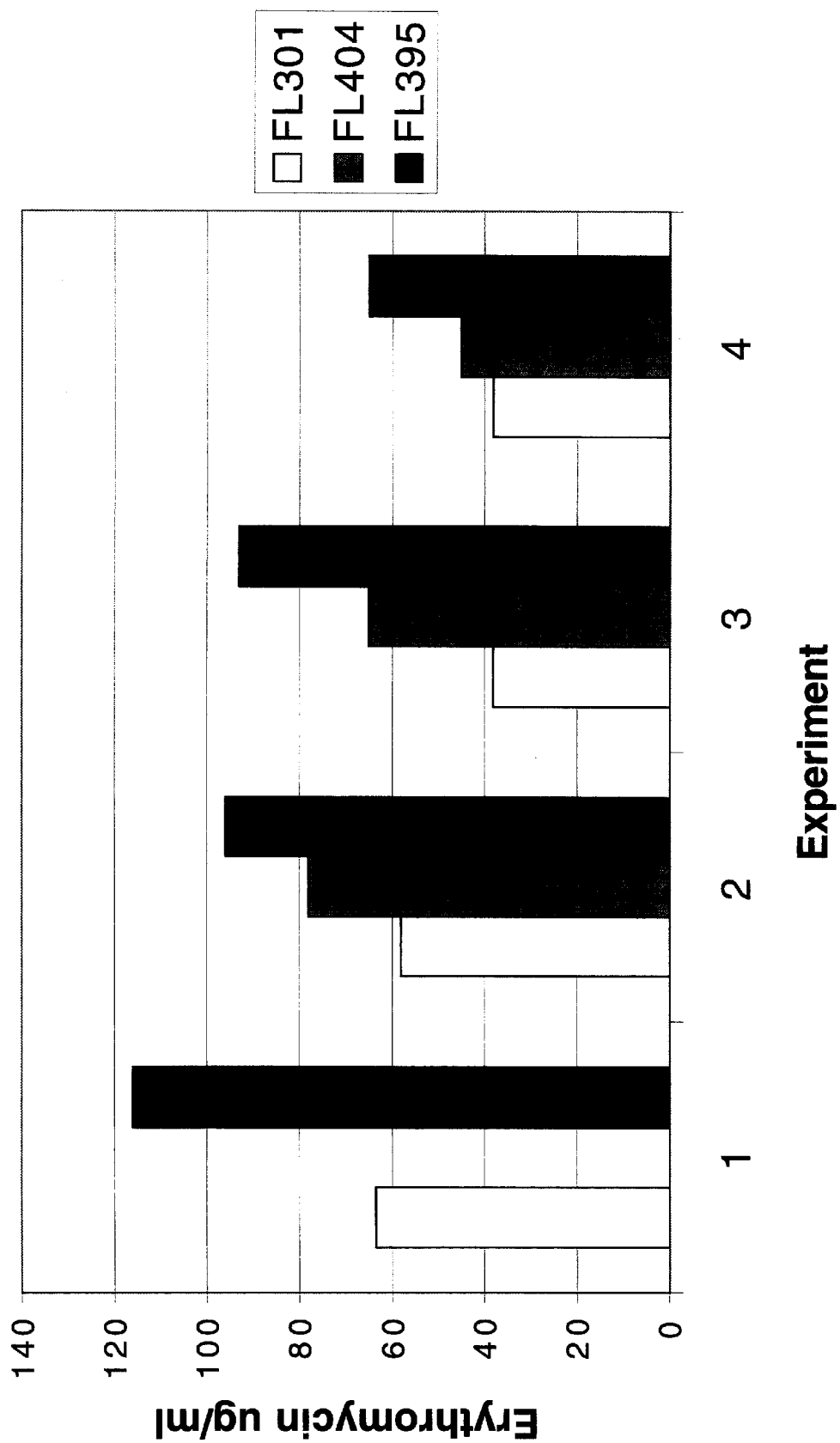

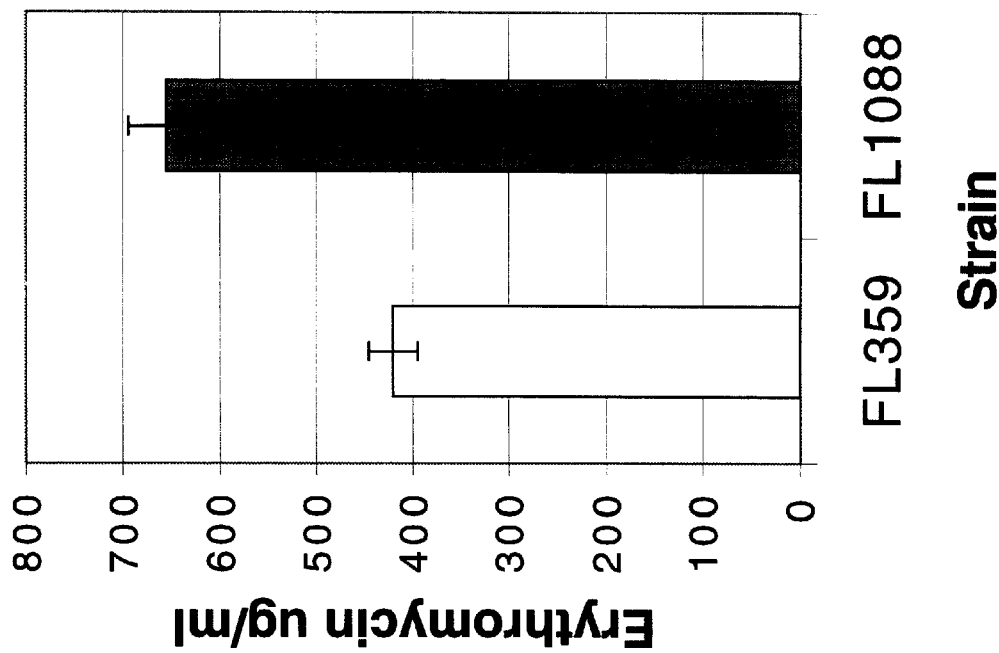

Figure 4A.

```
  1 GGATCATCTC CCAGATTTCT CCCACGGCAC CGGGGATGCC
 41 AACCGGCGCG CCGTCTCGCC CCGGCGGTTC GGGTCGGAAG
            SacI
 81 TCAAGAGCTC GGAAACCCGC CTTCGTCGTC ACCGCTGGCC
121 GCTCTCGCAC GCGCGTGCCA CGCGCGCGCG AGGCGACTGC
161 GTTTCCCAAG GTCGGAGTTC CGAGGTGCTA CCCGATTTCC
201 GACCCAGTTT CCGAGAGGCG CGCTCATGGC CGGCGCATGC
241 ACAGCGGGCC GGGGGTCACG CTTCGTGTTC CCTACTCGTT
281 TCCCTACTCG GTCTCCCTGA CGCCCTTTCC AGATGCGCCT
                                            SacI
                                            XhoI
321 ACGCGCGCGC CCGCGCGCGT GACGGTTGGC GCCCGCTCGA
                                            SacI
361 GCTCCCCGCC CACGAATCCC GATCTCGGCG AACACCGAGC
401 TCTCCGACGG GTTGCTGGTG TCCAGTAGA CGACGCGGTC
441 GGCGTTGCCC GCGCCCGAGC CGCACGCGGT GAGTGCGAGC
481 GCGCTGACCA GGCCGAGTGC GGCGACGGTG GCGGTGGCCT
521 TGGGTCTCAT GAGGCGGTGT CCTCCAGCT TTGCAAAAAC
561 TTGCGAGTAC CTGGCCGTAA ATTGCATACC CGAAACGTGA
601 GAAGAGTCAA GGTTTTTCGG ATGTTCACCG AACGAGCGCG
641 CCGGTCGTGT CAGGTCAACG TTTGCAAAAC ATTGCGCAAC
681 CGTGCAGGAT TGTGGCGCA ACACCGCCGT CGGCGAGGAG
            ClaI
721 GATCGATCTG AA
```

Figure 4B.

```
 733  GTG  GCG  GGT  CTG  TCG  GAT  ATC  GCC  AAG  GCT  GCC  GGA
  1▶  V    A    G    L    S    D    I    A    K    A    A    G
                      SalI-1
 769  GTC  AGC  GTG  TCG  ACG  GTC  AGC  CGG  GTG  CTC  AAC  CGC
 13▶  V    S    V    S    T    V    S    R    V    L    N    R
 805  CGG  GCG  GGC  ATC  AAG  GAG  GAC  ACC  CGC  CAG  CGC  GTG
 25▶  R    A    G    I    K    E    D    T    R    Q    R    V
 841  CTG  GCC  GTG  CTC  AAC  GAG  ATG  CCG  CAC  ACC  GCG  CGC
 37▶  L    A    V    L    N    E    M    P    H    T    A    R
 877  GGC  ATA  GGT  GCG  CTG  CGC  CGC  ACC  GGG  GTA  ATC  GGC
 49▶  G    I    G    A    L    R    R    T    G    V    I    G
 913  CTG  CTG  GTG  CCG  GAG  CTG  TCC  AAC  CCG  GTG  TTC  CCG
 61▶  L    L    V    P    E    L    S    N    P    V    F    P
 949  GCC  TTC  GCC  GAG  GCC  CTG  GAG  GCG  CGC  GCG  GTC  GGC
 73▶  A    F    A    E    A    L    E    A    R    A    V    G
 985  GCG  GGC  TAC  GCC  TCG  CTG  CTG  TGC  AAC  ACC  CGC  GTC
 85▶  A    G    Y    A    S    L    L    C    N    T    R    V
1021  GGG  ATG  AGC  GAG  GAG  GAC  TAC  GTC  CGG  ATG  CTC  ATC
 97▶  G    M    S    E    E    D    Y    V    R    M    L    I
1057  GCC  CGC  GGC  GTG  GAG  GGC  ATG  GTC  TTC  GTG  TCG  CCG
109▶  A    R    G    V    E    G    M    V    F    V    S    P
1093  GAG  ATC  GCC  AAC  ACC  GAG  GGC  GAG  CAG  CGG  ATC  AGC
121▶  E    I    A    N    T    E    G    E    Q    R    I    S
1129  CGC  AGC  TAC  TAC  GAG  AAG  CTG  CTG  GCC  GAC  GGC  GTG
133▶  R    S    Y    Y    E    K    L    L    A    D    G    V
1165  CGC  ATG  GTC  TTC  GTC  AAC  GGC  GGC  GCG  CCG  ACG  CTG
145▶  R    M    V    F    V    N    G    G    A    P    T    L
                                                    SalI-2
1201  GAC  GTG  CCC  GAC  GTC  GCC  GTC  GAC  GAG  CAC  CTG  GCC
157▶  D    V    P    D    V    A    V    D    E    H    L    A
1237  GGC  TAC  ACC  GCC  ACC  CGC  CAC  CTG  CTC  GAC  CTC  GGG
169▶  G    Y    T    A    T    R    H    L    L    D    L    G
1273  CAC  CGG  CGG  ATC  GGT  TTC  GTC  AGC  GGT  CCC  GCC  CGC
181▶  H    R    R    I    G    F    V    S    G    P    A    R
1309  GCG  GTG  CCC  TCG  CGG  CTC  AAG  CGC  GCA  GGC  TGG  GCC
193▶  A    V    P    S    R    L    K    R    A    G    W    A
1345  GCT  GCG  CTG  GAG  GAG  GCC  GAC  ATC  GCC  CCG  GAC  CCG
205▶  A    A    L    E    E    A    D    I    A    P    D    P
1381  CGG  CTG  GTC  GCG  CAC  GCG  CCG  TTC  GGC  GCG  GAG  GGC
217▶  R    L    V    A    H    A    P    F    G    A    E    G
```

Figure 4C.

```
                 NcoI
1417  GGC GCG CAG GCC ATG GCC GAG CTG CTC GAA ACC GCG
   1▶  G   A   Q   A   M   A   E   L   L   E   T   A
1453  GGC CCC ACC GCC GTG ATG TGC TCG TCG GAC GTC ATG
  13▶  G   P   T   A   V   M   C   S   S   D   V   M
1489  GCG CTC GGC GCG ATG CGC GAG GCC AAG CGG CGC GGA
  25▶  A   L   G   A   M   R   E   A   K   R   R   G
1525  CTG GCC ACC CCG GAG GAC CTG TCG GTG GTC GGC TTC
  37▶  L   A   T   P   E   D   L   S   V   V   G   F
1561  GAC GAC ATC GCG CTG GCC TCC TAC TGC CAG CCG GCG
  49▶  D   D   I   A   L   A   S   Y   C   Q   P   A
1597  CTG ACG ACG CTG GCG CAG CCG ATC GAG GAG ATG GCC
  61▶  L   T   T   L   A   Q   P   I   E   E   M   A
                                  SacI
1633  GCC GCG GCG GTG GAC GAG CTC TCC CGC CGC CTC GAC
  73▶  A   A   A   V   D   E   L   S   R   R   L   D
1669  CCG GAC CAG CCG GGC CGC GCG ACG ACG AGC TTC AGC
  85▶  P   D   Q   P   G   R   A   T   T   S   F   S
1705  CGG ATG TTC CGC CCG AAC CTG GTG GTG CGG GAG TCC
  97▶  R   M   F   R   P   N   L   V   V   R   E   S
1741  ACC GCC GCC CCG CGC TGA
 109▶  T   A   A   P   R   •
```

Figure 4D.

```
1759  CCGCGGCGGC  GGCGAATCGC  TTGCAGGAGA  AGTCGGAGTT
1799  CCGGCCTCCA  CGCGCGTGCG  CGCGGCCGGA  GCGCCACCGC
1839  CACATCGGCG  GGAACCGTGG  GAAGGGGTAC  TG GTG CTC AGG
                                           1▶  V   L   R
1880  GGT GCG GGA GTG CGC GGA ACG GCC GCC GAC TGG TGG
   4▶  G   A   G   V   R   G   T   A   A   D   W   W
1916  CGC GAC GCG GTG GTG TAC CAG GTC TAC GTC CGC AGC
  16▶  R   D   A   V   V   Y   Q   V   Y   V   R   S
1952  TTC GCC GAC GCC GAC GGC GAC GGG ATC GGC GAC CTG
  28▶  F   A   D   A   D   G   D   G   I   G   D   L
1988  GCG GGC GTG CGC GCA AGG CTG CCG TAC CTG GTG GAG
  40▶  A   G   V   R   A   R   L   P   Y   L   V   E
2024  CTG GGT GTG GAC GCG GTC TGG CTC ACG CCG TTC TAC
  52▶  L   G   V   D   A   V   W   L   T   P   F   Y
2060  CCG TCG CCG ATG GCC GAC GGC GGC TAC GAC GTC GCC
  64▶  P   S   P   M   A   D   G   G   Y   D   V   A
                           SalI-3
2096  GAC TAC TGC GAC GTC GAC CCG ATG TTC GGC ACG CTC
  76▶  D   Y   C   D   V   D   P   M   F   G   T   L
2132  GAC GAC TTC GAC GAC CTG CTG GCG CGG GCG CAC TCG
  88▶  D   D   F   D   D   L   L   A   R   A   H   S
                           SalI-4
2168  CTG GGC CTG AAG GTG ATC GTC GAC GTC GTG CCC AAC
 100▶  L   G   L   K   V   I   V   D   V   V   P   N
2204  CAC ACC TCC GAC GCG CAC CCG TGG TTC GCC GAG GCG
 112▶  H   T   S   D   A   H   P   W   F   A   E   A
                                                   KpnI
2240  CTG GAG GCC GGG CCG GGC GAC CCG GCG CGG GAG CGG
 124▶  L   E   A   G   P   G   D   P   A   R   E   R
2276  TAC CTG TTC CGC GAC GGG CGC GGC GAG AGC GGG GAG
 136▶  Y   L   F   R   D   G   R   G   E   S   G   E
2312  CTG CCG CCC AAC GAC TGG GAG TCA TCC TTC GGC GGT
 148▶  L   P   P   N   D   W   E   S   S   F   G   G
                                                   KpnI
2348  CCG GCG TGG ACC CGC GTC CCC GAC GGC CAG TGG TAC
 160▶  P   A   W   T   R   V   P   D   G   Q   W   Y
2384  CTG CAC CTG TTC GCC CCC GAG CAG CCC GAC CTG AAC
 172▶  L   H   L   F   A   P   E   Q   P   D   L   N
2420  TGG CGC AAC CCG CAG ATC CGC GCG GAG TTC GCC AAG
 184▶  W   R   N   P   Q   I   R   A   E   F   A   K
```

Figure 4E.

```
                                                        Sall-5
2456 GTG CTG GAG TTC TGG CTG GAC CGC GGG GTC GAC GGC
  1▶  V   L   E   F   W   L   D   R   G   V   D   G
2492 TTC CGG ATC GAC GTC GCC CAC GGC ATG ATC AAG CAC
 13▶  F   R   I   D   V   A   H   G   M   I   K   H
                                                    BglII
2528 CCC GAC CTG CCC GAC ACC GGG CTG CAC CAG CAG ATC
 25▶  P   D   L   P   D   T   G   L   H   Q   Q   I
2564 TCC CTG CTC GGC CGG GCC GAG CTG CCC TAC TTC GAC
 37▶  S   L   L   G   R   A   E   L   P   Y   F   D
2600 CAG GAC GAG GTG CAC GGC ATC TAC CGG GAG TGG CGC
 49▶  Q   D   E   V   H   G   I   Y   R   E   W   R
2636 GAG CTG CTG GAC TCC TAC GAG GGC GCC CGG ATC GGG
 61▶  E   L   L   D   S   Y   E   G   A   R   I   G
2672 GTG GCC GAG GCG TGG GCC CCG ACC AGT CAG CGC CTG
 73▶  V   A   E   A   W   A   P   T   S   Q   R   L
2708 GCC CGC TAC GTG CGC CCC GAC GAG CTG CAC CAG GCG
 85▶  A   R   Y   V   R   P   D   E   L   H   Q   A
2744 TTC AAC ATG GCG CTG CTG GAG TCG CCG TGG TCG GCC
 97▶  F   N   M   A   L   L   E   S   P   W   S   A
2780 GAC GGC TTC CGC GCG GTC ATC GAC GAC TCG CTC GCG
109▶  D   G   F   R   A   V   I   D   D   S   L   A
2816 GCC AAC GAC GCC GTC GGG GCC ACC ACG ACC TGG GTG
121▶  A   N   D   A   V   G   A   T   T   T   W   V
2852 CTG GGC AAC CAC GAC GTC AAG CGC CCG GTG ACC CGC
133▶  L   G   N   H   D   V   K   R   P   V   T   R
2888 TAC GGC GAC GGC GCC ACC GGC CTG CGC CGG GCG CGG
145▶  Y   G   D   G   A   T   G   L   R   R   A   R
2924 GCG GCG GCG CTG CTC AGC TTC GCG CTG CCG GGC TCG
157▶  A   A   A   L   L   S   F   A   L   P   G   S
2960 GTC TAC GTC TAC CAG GGG GAG GAG CTG GGG CTG CCG
169▶  V   Y   V   Y   Q   G   E   E   L   G   L   P
                                                 PstI
2996 GAG GTG CTG GAC CTG CCG GAG GAG GTG CTG CAG GAC
181▶  E   V   L   D   L   P   E   E   V   L   Q   D
3032 CCG GTG TGG GAG CGC TCC GGG CGC ACA GAC CGG GGC
193▶  P   V   W   E   R   S   G   R   T   D   R   G
3068 CGC GAC GGC TGC CGC GTG CCG ATG CCG TGG GAG GGT
205▶  R   D   G   C   R   V   P   M   P   W   E   G
3104 GCC GAC GCG CCG TTC GGG TTC GGT CCG GCC GGG AGC
217▶  A   D   A   P   F   G   F   G   P   A   G   S
```

Figure 4F.

```
3140 TGG CTG CCC GTC CCG CCC GGC TGG GCG CAG CTG TCG
  1▶  W   L   P   V   P   P   G   W   A   Q   L   S
3176 GTC GAG GCC CAG CGC GAG CGC GAC GAC TCG GTG CTG
 13▶  V   E   A   Q   R   E   R   D   D   S   V   L
     SalI-6                                      SacI
3212 TCG ACC TAC CGC AAG GCG CTC GCG CTG CGG CGA GAG
 25▶  S   T   Y   R   K   A   L   A   L   R   R   E
3248 CTC GGC TCG GAC GGT CTG GAG TGG ATG GAT GCC CCC
 37▶  L   G   S   D   G   L   E   W   M   D   A   P
3284 TCG GGC GTC CTT GCC TTC CGG CGC GGT CCC GGA CTG
 49▶  S   G   V   L   A   F   R   R   G   P   G   L
3320 GTG TGC GCG GTG AAC TTC GGT TCC GAA CCG GTG TCG
 61▶  V   C   A   V   N   F   G   S   E   P   V   S
3356 CTG GAC CTG CCG GGA CGG CTG CTG TGC CGC AGC GAC
 73▶  L   D   L   P   G   R   L   L   C   R   S   D
3392 GCG GGC GCC GAC TGG TCG GGT GTG CTA CCG GGC GAC
 85▶  A   G   A   D   W   S   G   V   L   P   G   D
3428 ACC GCC GTC TGG CTG GCG GGC TGA
 97▶  T   A   V   W   L   A   G   •
```

Figure 4G.

```
3452 GCGGGAGGCC CGGCGGGGAA GGATTCACCG AGAATCCTCC
                                                        ClaI
3492 CAATAGGTCT ATTTCTTGCC GGACCGGCGT GGTCACATCG
3532 ATACCCCCTG CACACGAGGA GGTAGTCG ATG ACC ATC TTG
                                          1▶  M   T   I   L
3572 CGG CGA TTA GCC GTC GGC GCC GCG GCA CTG GCG CTC
  5▶  R   R   L   A   V   G   A   A   A   L   A   L
3608 GCG GGG TTG GGC GTG GTC GGC ATC GGG CAG ACG CCC
 17▶  A   G   L   G   V   V   G   I   G   Q   T   P
3644 GCG TCG GCC GCG CCC AAC TTC CAG GTG CCC TTC GCC
 29▶  A   S   A   A   P   N   F   Q   V   P   F   A
3680 TGC GGT GTC ACC GTC ACC GCG GCC ACG TTC AGC GGC
 41▶  C   G   V   T   V   T   A   A   T   F   S   G
                                 SalI-7
3716 CAC AAC CCG CCC AAC TCG GTC GAC TTC CAG AAG AGC
 53▶  H   N   P   P   N   S   V   D   F   Q   K   S
3752 GGC ATC ACC GGC ATG CCG GTG CTC GCA TCC GCC GCG
 65▶  G   I   T   G   M   P   V   L   A   S   A   A
3788 GGC AAG ATC ACC AGG GTG GCC AAC GAG GGC GAC ACC
 77▶  G   K   I   T   R   V   A   N   E   G   D   T
3824 AGC TAC GGG CGA TGG GTC GAG ATC GAC CAC GGT GCC
 89▶  S   Y   G   R   W   V   E   I   D   H   G   A
3860 GGC TGG ACC ACC CGC TAC GCG CAC CTG AAC AGC CAG
101▶  G   W   T   T   R   Y   A   H   L   N   S   Q
3896 ACC GTC TCG GTC GGC CAG CAG GTC GCG CTC GGC GCC
113▶  T   V   S   V   G   Q   Q   V   A   L   G   A
3932 AAG ATC GGC ACC GCC GGT GCG ACC GGC GGC GTG ACC
125▶  K   I   G   T   A   G   A   T   G   G   V   T
3968 GGG CCC CAC CTG CAC TAC GAA CAG CGC CTC AAC GGC
137▶  G   P   H   L   H   Y   E   Q   R   L   N   G
4004 ACC GCG CAG AAG GCC AAG CTC AAC GGC GTC GCG GTC
149▶  T   A   Q   K   A   K   L   N   G   V   A   V
4040 CCG TAC TAC GGC CAC ACC GAC TTC ACC AGC AAG AAC
161▶  P   Y   Y   G   H   T   D   F   T   S   K   N
      PstI
4076 AAC TGC AGC GGC AAC CCC TAC ACG CCG ACC GAG GTG
173▶  N   C   S   G   N   P   Y   T   P   T   E   V
4112 TGC GGC GCC GGC TAC AGC GTG ATC GAC CAG CAG GCG
185▶  C   G   A   G   Y   S   V   I   D   Q   Q   A
4148 CTG GGC GGC GCG GGC ACC ACC TAC CTG CTC TAC AAC
197▶  L   G   G   A   G   T   T   Y   L   L   Y   N
4184 GCG TCC AAC GCC GGC AAC TGC GTG GTC ACG CTG AAG
209▶  A   S   N   A   G   N   C   V   V   T   L   K
```

Figure 4H.

```
4220  GCC  AGG  TCG  CTG  GGC  ACC  GCG  ACG  GCG  ACC  TCG  GCG
   1▶  A    R    S    L    G    T    A    T    A    T    S    A
4256  TTC  CTG  GAG  GTC  GAG  GGG  ACC  GCG  CGG  GTC  ACC  GAC
  13▶  F    L    E    V    E    G    T    A    R    V    T    D
4292  AGC  GGC  AAC  TTC  ACC  TAC  TAC  GCG  GGC  CCG  GTG  CGC
  25▶  S    G    N    F    T    Y    Y    A    G    P    V    R
4328  AAG  GTC  GCC  GAG  GCC  ACC  TGC  GTG  AAG  TGG  GGC  GGC
  37▶  K    V    A    E    A    T    C    V    K    W    G    G
4364  TCG  GTC  GGT  TCG  GAG  TCC  TAC  ACC  AGC  CCG  TTC  GAG
  49▶  S    V    G    S    E    S    Y    T    S    P    F    E
4400  CAC  TGC  GGC  TAG
  61▶  H    C    G    •
```

Figure 4I.

```
4412  GCAGAACCTC  GTTGCTGTCC  TTGAACTCGC  CTTGCGTGGC
4452  GGTTCCGGTG  GCGGAACCTC  AGGCGTCCTC  TGGCTCCGGG
4492  ACCTTTTTCT  GACGTATGCC  CATACGCTGC  GAAAAAGCTG
4532  TCCTCGCCAG  AGGACGCCTG  AGAACCCGCG  GCGGTGCGGG
4572  TTGCGGGGTG  GGCCAAGCGG  CTGCGCCGCT  TCAAAGACCT  G C
                                                      54◀
4614  TA  GAA  GAC  GGA  CCA  GCC  GGT  CAG  CGT  GGT  GAA  GTG
 53◀•     F    V    S    W    G    T    L    T    T    F    H
4649  GTC  GAG  GGC  GGC  AAC  GCC  CGC  CAC  CGA  GTT  GCC  GCG
 42◀  D    L    A    A    V    G    A    V    S    N    G    R
4685  CCG  GTC  CAG  GCC  GGG  GCT  CCA  CAC  CGC  GAC  CGC  GCA
 30◀  R    D    L    G    P    S    W    V    A    V    A    C
4721  GCG  GCC  CGG  CAC  GAT  CGC  CAG  GAT  GCC  GCC  GCC  GAC
 18◀  R    G    P    V    I    A    L    I    G    G    G    V
4757  GCC  GCT  CTT  GCC  CGG  GAT  CC
  6◀  G    S    K    G    P    I
```

METHODS AND COMPOSITIONS FOR ENHANCING ERYTHROMYCIN PRODUCTION

TECHNICAL FIELD OF THE INVENTION

The field of the invention is antibiotic production. More particularly the present invention relates to compositions and methods for enhancing erythromycin production in bacterial cells.

BACKGROUND OF THE INVENTION

Erythromycin A (Em) is a medically important antibiotic produced by fermentation of the Actinomycete *Saccharopolyspora erythraea* (Bunch and McGuire 1953). More recently it has also become increasingly used as the chemical starting point for the generation of a new generation of semi-synthetic macrolide derivatives which has created a demand for the production of larger quantities of this bulk compound. In the past, increasing product output from well-developed fermentation processes involved either increasing the size of the fermentation plant, or using the traditional empirical mutate-and-screen approach to strain improvement (Queener and Lively, 1986). Because commercial scale fermentors are very costly and the traditional strain improvement methods do not reliably result in significantly better strains, a rational approach to strain improvement involving metabolic engineering of antibiotic producing organisms has been developed. The approach involves using genetic engineering to increase the expression of positive regulators of antibiotic production.

To find positive regulators of erythromycin projection from *Sac. erythraea* a protocol involving a simple visual screen that has been used successfully in the past for the isolation of antibiotic regulatory genes from other Actinomycete species was followed(Horinouchi et al., 1983; Horihouchi and Beppu, 1984). A slightly different method than Horinuchi and et al. (1983) and others since then was used (Romero, et al., 1992; Fernandez-Moreno et al., 1992; Ishizuka et al., 1992) to discover genes from *Sac. erythraea* that were different from any of those previously found to stimulate antibiotic production in other Actinomycetes (Chater and Bibb, 1997). The present invention describes the cloning and characterization of a DNA fragment carried by pFL37 which contains two genes involved in starch utilization and one new regulatory gene.

BRIEF SUMMARY OF THE INVENTION

In one aspect, the present invention provides an isolated and purified polynucleotide. That polynucleotide includes: (a) the nucleotide sequence of SEQ ID NO:1 from nucleotide number 733 to nucleotide number 1758, the nucleotide sequence of SEQ ID NO:1 from nucleotide number 1889 to nucleotide number 3451, or the nucleotide sequence of SEQ ID NO:1 from nucleotide number 3560 to nucleotide number 4411: (b) sequences that are complementary to the sequence of (a); and sequences that hybridize under stringent condition to the sequence of (a) and, which on expression produce a polypeptide that contains the polypeptide encoded by the sequence of (a).

The polynucleotide can be a DNA molecule or an RNA molecule. In specific embodiments, the polynucleotide has (a) the nucleotide sequence of SEQ ID NO:1 from nucleotide number 733 to nucleotide number 3451; (b) the nucleotide sequence of SEQ ID NO:1 from nucleotide number 733 to nucleotide number 4411; (c) both the nucleotide sequence of SEQ ID NO:1 from nucleotide number 733 to nucleotide number 1758 and the nucleotide sequence of SEQ ID NO:1 from nucleotide number 1889 to nucleotide number 3451; (d) both the nucleotide sequence of SEQ ID NO:1 from nucleotide number 733 to nucleotide number 1758 and the nucleotide sequence of SEQ ID NO:1 from nucleotide number 3560 to nucleotide number 4411; (e) both the nucleotide sequence of SEQ ID NO:1 from nucleotide number 1899 to nucleotide number 3451 and the nucleotide sequence of SEQ ID NO:1 from nucleotide number 3560 to nucleotide number 4411; (f) the nucleotide sequence of SEQ ID NO:1 from nucleotide number 733 to nucleotide number 1758, the nucleotide sequence of SEQ ID NO:1 from nucleotide number 1889 to nucleotide number 3451, and the nucleotide sequence of SEQ ID NO:1 from nucleotide number 3560 to nucleotide number 4411; or (g) the nucleotide sequence of SEQ ID NO:1. The present invention further provides an expression vector comprising a polynucleotide of the invention. The expression vector drives expression of the polynucleotide in a cell. Preferred polynucleotides are set forth above. A bacterial host cell transformed with a polynucleotide of the invention is also provided.

The host cells can be used to make polypeptides that enhance antibiotic production. In accordance with this aspect, a suitable host cell is transformed with an expression vector of the invention and maintained under conditions and for a period of time sufficient for production of the polypeptide. Polypeptides produced by such a process are also provided.

In another aspect, the present inventor provides isolated and purified polypeptides that enhance antibiotic production in bacterial cells. Exemplary and preferred such polypeptides comprise the amino acid residue sequences of SEQ ID Nos: 2, 3, and/or 4.

In yet another aspect, the present invention provides a process of enhancing the production of erthromycin in a bacterial cell that produces erythromycin. The process includes the step of increasing the levels of polypeptides of this invention in the cell. The bacterial cell is preferably a *Sac. erythraea*. The polypeptide levels are preferably increased by transforming the cell with a polynucleotide that contains the nucleotide sequence of SEQ ID NO:1 from nucleotide number 733 to nucleotide number 1752, the nucleotide sequence of SEQ ID NO:1 from nucleotide number 1889 to nucleotide number 3451, and the nucleotide sequence of SEQ ID NO:1 from nucleotide number 3560 to nucleotide number 4411.

Figure 1:
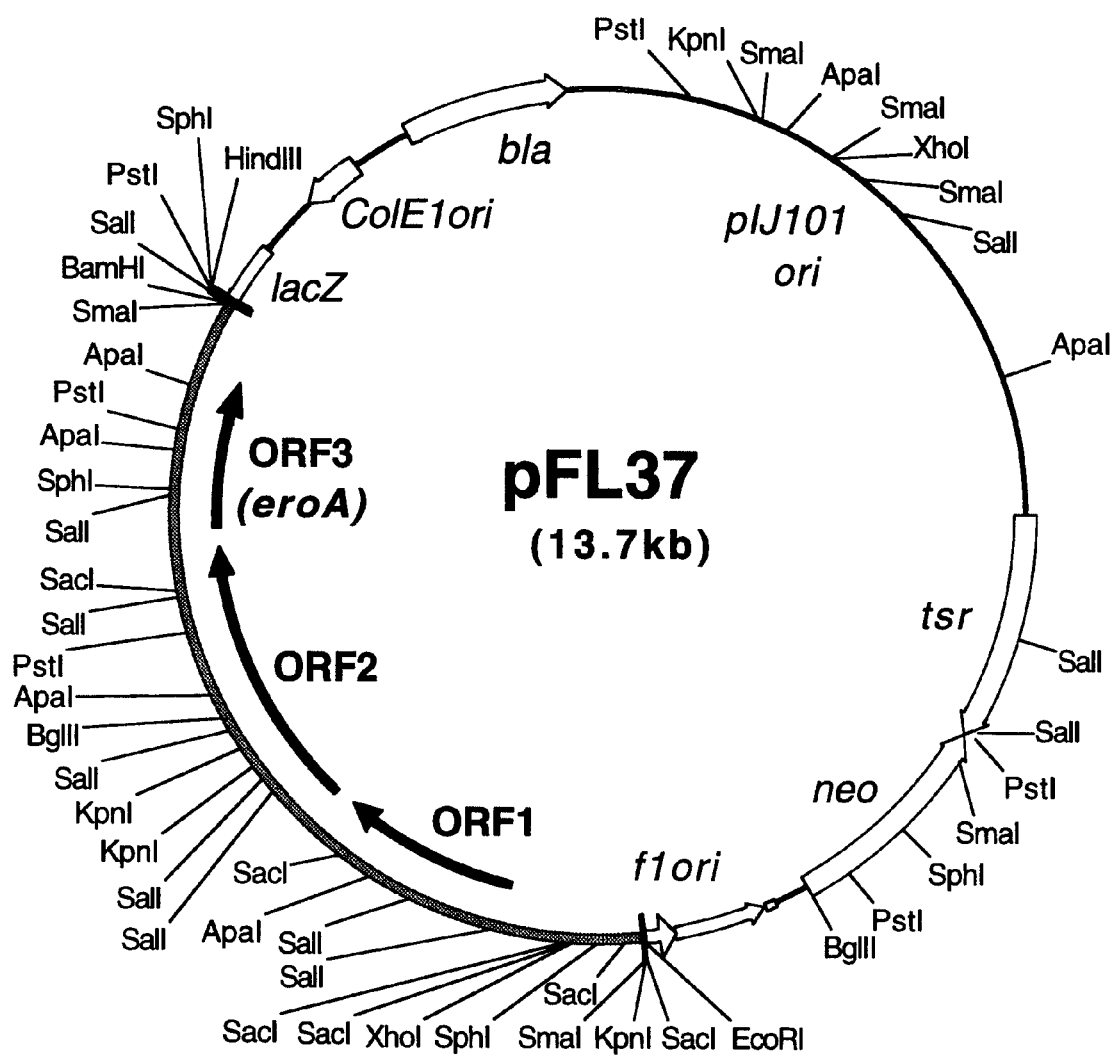
FIG. 1. Shows a map of pFL37. The following features are shown: bla, ampicillin resistance; tsr, thiostrepton resistance; neo, the promoterless kamamycin-resistance gene; lac, disrupted β-galactosidase gene; colElori, *E. coli* origin of replication; pIJ101ori, Streptomyces origin of replication; ORF1–3, cloned fragement of DNA from *Sac. erythraea* that stimulate production of erythromycin.

FIG. 3(a) and FIG. 3(b) show *Sac. erythraea* shake flask fermentation results. FIG. 3A Unshaded bars, red variant strain; lightly shaded bars, pFL37 transformants, and dark shaded bars, pFL37 amplified transformants. Media used for Experiment No. 1 was E29F with 4× starch and 0.3× oil, using the fermentation protocol described in Examples. Experiments No. 2–4 were performed with E29F medium without oil. Each bar is an average from the results of four independent shake flasks. FIG. 3B Unshaded bar is the wild type (White) strain. Shaded bar is the pFL37 integrated transformant of the White strain. Medium was E29F with oil. Fermentation conditions were 32° C., 5 days, in shake flask fermentation.

FIG. 4A–FIG. 4I shows the nucleotide sequence of the 4,776 bp cloned fragment in pFL37 and the deduced amino acid sequence. The numbers of the nucleotides and amino acids are shown to the left. Putative ribosome binding sites are in italics. The rare TTA codon of ORF3 is boxed. SalI sites that were used for insertional mutagenesis with the aphA1 gene are numbered corresponding to the reference numbers used on darts in FIG. 2.

DETAILED DESCRIPTION OF THE INVENTION

I. The Invention

The present invention provides isolated and purified polypeptides that increase antibiotic production, polynucleotides that encode those polypeptides, expression vectors containing those polynucleotides, host cells transformed with those expression vectors, a process of making the polypeptides using those polynucleotides and vectors, and processes using those polypeptides and polynucleotides.

II. Polypeptides

In one aspect, the present invention provides one or more polypeptides that enhance antibiotic production in bacterial cells capable of making the antibiotic. Polypeptides of the present invention are particularly useful in enhancing the production of erythromycin in the *Saccharospolyspora erythraea* (*Sac. erythraea*).

The present invention provides 3 separate polypeptide gene products that act alone or in combination to enhance antibiotic production. The 3 polypeptides are encoded by a region of polynucleotides disclosed herein designated ORF1, ORF2, ORF3. The polypeptides encoded by ORF1 contains 340 amino acid residues. The amino acid residue sequence of that polypeptide is referred to herein as SEQ ID NO: 2. ORF2 encodes a polypeptide that contains 526 amino acid residues. The amino acid residue sequence of the product of ORF2 is referred to herein as SEQ ID NO: 3. ORF3 encodes a polypeptide containing 283 amino acid residues. The amino acid residue sequence of the product of ORF3 is referred to herein as SEQ ID NO: 4. As set forth hereinafter, any of these polypeptides, either alone or in combination, can enhance the production of antibiotics when administered to cells capable of producing that antibiotic. Combinations of polypeptides include a combination of the polypeptide of SEQ ID NO: 2 with SEQ ID NO: 3; a combination of the polypeptide of SEQ ID NO: 2 with the polypeptide of SEQ ID NO:4; a combination of the polypeptide of SEQ ID NO:3 and the polypeptide of SEQ ID NO: 4; and a combination of all three, the polypeptides of SEQ ID Nos.:2, 3 and 4.

The present invention also contemplates amino acid residue sequences that are substantially duplicative of the sequences set forth herein such that those sequences demonstrate like biological activity to disclosed sequences. Such contemplated sequences include those sequences characterized by a minimal change in amino acid residue sequence or type (e.g., conservatively substituted sequences) which insubstantial change does not alter the basic nature and biological activity of the polypeptides.

It is well known in the art that modifications and changes can be made in the structure of a polypeptide without substantially altering the biological function of that peptide. For example, certain amino acids can be substituted for other amino acids in a given polypeptide without any appreciable loss of function. In making such changes, substitutions of like amino acid residues can be made on the basis of relative similarity of side-chain substituents, for example, their size, charge, hydrophobicity, hydrophilicity, and the like.

As detailed in U.S. Pat. No. 4,554,101, incorporated herein by reference, the following hydrophilicity values have been assigned to amino acid residues: Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4). It is understood that an amino acid residue can be substituted for another having a similar hydrophilicity value (e.g., within a value of plus or minus 2.0) and still obtain a biologically equivalent polypeptide.

In a similar manner, substitutions can be made on the basis of similarity in hydropathic index. Each amino acid residue has been assigned a hydropathic index on the basis of its hydrophobicity and charge characteristics. Those hydropathic index values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5). In making a substitution based on the hydropathic index, a value of within plus or minus 2.0 is preferred.

III. Polynucleotides

In another aspect, the present invention provides isolated and purified polynucleotides that encodes polypeptides of the present invention. The polynucleotide can be a DNA molecule (e.g., gene sequence, cDNA) or an RNA molecule (e.g., mRNA).

The present invention also provides non-coding strands that are complementary to the coding sequences as well as RNA sequences identical to or complementary to those coding sequences. One of ordinary skill will readily appreciate that corresponding RNA sequences contain uracil (U) in place of thymidine (T).

In one embodiment, a polynucleotide of the present invention is an isolated and purified DNA molecule that contains a coding sequence for one or more polypeptides of this invention. An exemplary such DNA molecule is shown as SEQ ID NO: 1. Preferred polynucleotides of this invention depend on the specific polypeptide preferred.

By way of example, where the polypeptide contains the amino acid residue sequence of SEQ ID NO:2 a preferred polynucleotide contains the nucleotide sequence of SEQ ID NO:1 from nucleotide number 733 to nucleotide number 1758. Where the polypeptide contains the amino acid residue sequence of SEQ ID NO:3 a preferred polynucleotide contains the nucleotide sequence of SEQ ID NO:1 from nucleotide number 1889 to nucleotide number 3451. Where the polypeptide contains the amino acid residue sequence of SEQ ID NO:4 a preferred polynucleotide contains the nucleotide sequence of SEQ ID NO:1 from nucleotide number 3560 to nucleotide number 4411. Where the polypeptide contains the amino acid residue sequence of SEQ ID NOS:2, 3 and 4, a preferred polynucleotide contains the nucleotide sequence of SEQ ID NO:1 from nucleotide number 733 to nucleotide number 3451. Where the polypeptide contains the amino acid residue sequences of SEQ ID NOS: 3 and 4, a preferred polynucleotide contains nucleotide sequence of SEQ ID NO: 1 from nucleotide number 1889 to nucleotide number 4411. Where the polypeptide contains the amino acid residue sequences of SEQ ID NO: 2 and 4, a preferred polynucleotide contains the nucleotides sequence of SEQ ID NO:1 from nucleotide number 733 to nucleotide 1758 and from nucleotides number 3560 to nucleotide number 4411. Where the polypeptides contains the amino acid residue sequences of SEQ ID Nos: 2 and 3, the polynucleotide contains the nucleotide sequences of SEQ ID No:1 from nucleotide number 733 to nucleotide number 1758 and from nucleotide number 1889 to nucleotide number 3451.

The present invention also contemplates DNA sequences which hybridize under stringent hybridization conditions to the DNA sequences set forth above. Stringent hybridization conditions are well known in the art and define a degree of sequence identity greater than about 70%–80%. The present invention also contemplates naturally occurring allelic variations and mutations of the DNA sequences set forth above so long as those variations and mutations code, on expression, for a polypeptide of this invention as set forth hereinbefore.

As is well known in the art, because of the degeneracy of the genetic code, there are numerous other DNA and RNA molecules that can code for the same polypeptides as those encoded by SEQ ID NO:1, or portions thereof. The present invention, therefore, contemplates those other DNA and RNA molecules which, on expression, encode for a polypeptide that contains one or more polypeptides encoded by SEQ ID NO: 1, or portions thereof as set forth above. Having identified the amino acid residue sequence those polypeptides, and with knowledge of all triplet codons for each particular amino acid residue, it is possible to describe all such encoding RNA and DNA sequences. DNA and RNA molecules other than those specifically disclosed herein and, which molecules are characterized simply by a change in a codon for a particular amino acid are within the scope of this invention.

A Table of codons representing particular amino acids is set forth below in Table 1.

TABLE 1

| First position | Second Position | | | | Third position |
|---|---|---|---|---|---|
| (5' end) | T/U | C | A | G | (3' end) |
| T/U | Phe | Ser | Tyr | Cys | T/U |
|  | Phe | Ser | Tyr | Cys | C |
|  | Leu | Ser | Stop | Stop | A |
|  | Leu | Ser | Stop | Trp | G |
| C | Leu | Pro | His | Arg | T/U |
|  | Leu | Pro | His | Arg | C |
|  | Leu | Pro | Gln | Arg | A |
|  | Leu | Pro | Gln | Arg | G |
| A | Ile | Thr | Asn | Ser | T/U |

TABLE 1-continued

| First position | Second Position | | | | Third position |
|---|---|---|---|---|---|
| (5' end) | T/U | C | A | G | (3' end) |
|  | Ile | Thr | Asn | Ser | C |
|  | Ile | Thr | Lys | Arg | A |
|  | Met | Thr | Lys | Arg | G |
| G | Val | Ala | Asp | Gly | T/U |
|  | Val | Ala | Asp | Gly | C |
|  | Val | Ala | Glu | Gly | A |
|  | Val | Ala | Glu | Gly | G |

A simple change in a codon for the same amino acid residue within a polynucleotide will not change the structure of the encoded polypeptide. By way of example, it can be seen from SEQ ID NO: 1 that a TCG codon for serine exists at nucleotide positions 745–747 and at positions 1097–1099. It can also be seen from that same sequence, however, that serine can be encoded by a AGC codon (see e.g., nucleotide positions 1125–1127 and 1131–1133). Substitution of the latter AGC codon for serine with the TCA codon for serine, or visa versa, does not substantially alter the DNA sequence of SEQ ID NO: 1 and results in expression of the same polypeptide. In a similar manner, substitutions of codons for other amino acid residues can be made in a like manner without departing from the true scope of the present invention.

A polynucleotide of the present invention can also be an RNA molecule. A RNA molecule contemplated by the present invention is complementary to or hybridizes under stringent conditions to any of the DNA sequences set forth above. As is well known in the art, such a RNA molecule is characterized by the base uracil in place of thymidine. Exemplary and preferred RNA molecules are mRNA molecules that encode an adenosine kinase of this invention.

IV. Oligonucleotides

The present invention also contemplates oligonucleotides from about 15 to about 50 nucleotides in length, which oligonucleotides serve as primers and hybridization probes for the screening of DNA libraries and the identification of DNA or RNA molecules that encode other polypeptides involved on regulating antibiotic production. Such primers and probes are characterized in that they will hybridize to polynucleotide sequences encoding a polypeptide of this invention. An oligonucleotide probe or primer contains a nucleotide sequence that is identical to or complementary to a contiguous sequence of at least 15 nucleotides polynucleotide of the present invention. Thus, where an oligonucleotide probe is 25 nucleotides in length, at least 15 of those nucleotides are identical or complementary to a sequence of contiguous nucleotides of a polynucleotide of the present invention.

A preferred oligonucleotide is an antisense oligonucleotide. The present invention provides a synthetic antisense oligonucleotide of less than about 50 nucleotides, preferably less than about 35 nucleotides, more preferably less than about 25 nucleotides and most preferably less than about 20 nucleotides. An antisense oligonucleotide of the present invention is directed against a DNA or RNA molecule that encodes a polypeptide of the present invention. Preferably, the antisense oligonucleotide is directed against the translational initiation site or the transcriptional start site. It is understood by one of ordinary skill in the art that antisense oligonucleotide can be directed either against a DNA or RNA sequence that encodes a specific target. Thus, an antisense oligonucleotide of the present invention can also be directed against polynucleotides that are complementary to those shown in SEQ. ID NO: 1 as well as the equivalent RNA molecules.

Preferably, the nucleotides of an antisense oligonucleotides are linked by pseudophosphate bonds that are resistant to clevage by exonuclease or endonuclease enzymes. Preferably the pseudophosphate bonds are phosphorothioate bonds. By replacing a phosphodiester bond with one that is resistant to the action of exo- and/or endonuclease, the stability of the nucleic acid in the presence of those enzymes is increased. As used herein, pseudophosphate bonds include, but are not limited to, methylphosphonate, phosphomorpholidate, phosphorothioate, phosphorodithioate and phosphoroselenoate bonds.

An oligonucleotide primer or probe, as well as an antisense oligonucleotide of the present invention can be prepared using standard procedures well known in the art. A preferred method of polynucleotide synthesis is via cyanoethyl phosphoramidite chemistry. A detailed description of the preparation, isolation and purification of polynucleotides is set forth below.

V. Expression Vectors and Transformed Cells

The present invention further provides expression vectors e.g., (FIG. 1) that contain a polynucleotide of the invention and host cells transformed or transfected with those polynucleotides or expression vectors.

A polynucleotide that encodes one or more polypeptides of the invention is placed into an expression vector suitable for a given host cell such that the vector drives expression of the polynucleotide(s) in that host cell. Vectors for use in particular cells are well known in the art and include phage or plasmids.

In one embodiment, a host cell is an eukaryotic host cell and an expression vector is an eukaryotic expression vector (i.e., a vector capable of directing expression in a eukaryotic cell). Such eukaryotic expression vectors are well known in the art. In another embodiment, the host cell is a bacterial cell. The bacterial host cell is capable of producing an antibiotic. A preferred antibiotic is erythromycin. Bacterial cells that make erythromycin are well known in the art. An exemplary and preferred bacterial cell is an Actinomycete and more preferably, a *Sac. erythraea*.

A polynucleotide of an expression vector of the present invention is preferably operatively associated or linked with an one or more promoters. A promoter is a region of a DNA molecule typically within about 100 nucleotide pairs in front of (upstream of) the point at which transcription begins. That region typically contains several types of DNA sequence elements that are located in similar relative positions in different genes. As used herein, the term "promoter" includes what is referred to in the art as an upstream promoter region or a promoter of a generalized RNA polymerase transcription unit.

A promoter is operatively linked to a coding sequence that encodes at least one gene product. As used herein, the phrase "operatively linked" or its gramatical equivalent means that a regulatory sequence element (e.g. a promoter or transcription terminating region) is connected to a coding sequence in such a way that the transcription of that coding sequence is controlled and regulated by that promoter. Means for operatively linking a promoter to a coding sequence are well known in the art.

A promoter used in an expression vector of the present invention can be any promoter that drives expression in a host cell. By employing a promoter with well known properties, the level of expression can be optimized. For example, selection of a promoter that is active in specifically transformed cells permits high level expression of the desired product. Still further, selection of a promoter that is regulated in response to a specific physiological signal can permit inducible expression.

The placement of a promoter sequence relative to an encoding sequence of an expression vector will depend as is known in the art on whether the encoding sequence encodes one or more of the polypeptides as set forth above. By way of example, each encoding sequence can be operatively associated with a separate promoter sequence. Alternately, as shown with SEQ. ID NO 1., a single promoter sequence can be operatively linked with only one of the encoding DNA sequences (e.g. ORF1, ORF2, and ORF3).

A coding sequence of an expression vector may be linked to a transcription terminating region. Typically, DNA sequences located a few hundred base pairs downstream of the ORF serve to terminate transcription. Those DNA sequences are referred to herein as transcription-termination regions. Promoters and transcription-terminating regions are well known in the art. The selection of a particular enhancer-promoter or transcription-terminating region will depend, as is also well known in the art, on the cell to be transformed.

VI. Method of Making Polypeptide

In another aspect, the present invention provides a process of making one or more polypeptides of the present invention. In accordance with that process, a suitable host cell is transformed with a polynucleotide of the present invention. The transformed cell is maintained for a period of time sufficient for expression of the polypeptide. The formed polypeptide can be recovered. Preferably, the polynucleotide is contained in an expression vector as set forth above.

VII. A Process of Using Polypeptides and Polynucleotides of the Present Invention In another aspect, the present invention provides uses for the polypeptides and polynucleotides of the present invention. Those polynucleotides and polypeptides are used to enhance antibiotic production in cells capable of producing that antibiotic. Typically, compositions of the present invention are used to enhance antibiotic production in bacterial cells transformed with genes that allow for expression and production of a given antibiotic.

Antibiotic production in a cell is increased by exposing the cell to increased levels of one or more polypeptides of the present invention. In a preferred embodiment, the cell is exposed to a solution (e.g., culture media) that contains effective stimulatory amounts of those polypeptides. Preferably, that solution contains effective stimulating amounts of more than one polypeptide of the present invention. Even more preferably, that solution contains effective stimulating amounts of the polypeptides having the amino acid residue sequences of SEQ ID Nos: 2, 3 and 4.

Levels of those polypeptides can be increased in an antibiotic producing cell by increasing the expression of a polynucleotide that encodes those polypeptides. In accordance with this embodiment, the cell is transformed with an expression vector that contains polynucleotides that encode those polypeptides and which expression vectors will drive the expression of those polynucleotides. In a preferred embodiment, the levels of polypeptides are increased by transforming cells with expression vectors containing polynucleotides that encode more than one polypeptide of the present invention. Most preferably, the expression vector contains polynucleotides that encode all three polypeptides of the present invention. Polynucleotides and polypeptides of the present invention are particularly useful for increasing the production of the antibiotic erthromycin in *Sac. erythraea*.

As disclosed herein, a DNA clone from *Sac. erythraea* causes a significant and reproducible increase in production of erythromycin when it is introduced into the chromosome of this strain in multiple copies. This represents the first rational approach to the construction of higher erythromycin-producing stains. Previously, erythromycin yield improvements relied on traditional mutagenesis and screening methods (Queener and Lively, 1986).

Although much recent work has appeared concerning the molecular genetics of erythromycin biosynthesis, the work has focused on the erythromycin biosynthetic gene cluster, and very little is known about the regulation of these genes. A visual screening method (Horinouchi and Beppu, 1984), which had been shown to be useful for identifying heterologous activators of actinorhodin production in *S. lividans*, was used to identify activators of blue pigment formation, and stimulate erythromycin production in *Sac. erythraea*.

This approach allowed for the screening of a large library of DNA fragments covering the entire genome of *Sac. erythraea*. One of the factors that aided in the identification of the clone in pFL37, which contained a novel regulatory gene, was the composition of the agar used for screening the library. Previous investigators had used, for example, Bennet's Agar (Horinouchi and Beppu, 1984), or standard Streptomyces media (Romero et al, 1992).

The *S. lividans* prescreen was therefore helpful in finding our novel genes, but upon careful characterization of these genes we found that the genes behaved differently in the two hosts studied. For example, in *Sac. erythraea*, neither thiostrepton nor starch were required for the induction of erythromycin overproduction, but both were required for the stimulation of actinorhodin production in *S. lividans*. Since erythromycin overproduction apparently involves both ORF2 and the ORF3 gene, the situation seems to be more complicated in *Sac. erythraea* than in *S. lividans*. In *S. lividans* it is clear that only the ORF3 gene is required for stimulation of actinorhodin production and grey spore formation.

pFL37 is useful for strain improvement as an integrative plasmid. In its present form the plasmid can be directly transformed and tested in any commercial erythromycin producing strain. "Second generation" constructions can be used for the overexpression of the genes on pFL37 for production improvements. In both the first generation and second generation formats, there is no need for introducing modifications to the existing commercial process. For example, the addition of thiostrepton for the maintenance of the plasmid is not necessary. The plasmid in its amplified form is also stable for the period of the fermentation without having to add selective pressure.

The Examples to follow illustrate preferred embodiments of the present invention and are not limiting of the specification and claims in any way.

EXAMPLE 1

General Methods

Bacterial strains and plasmids

*Streptomyces lividans* TK21 (Hopwood et al., 1985) was the host strain in transformations. *Saccharopolyspora erythraea* ATCC 11635 (red varient) was the source of genomic DNA used for the generation of the DNA fragment library. The *E. coli* DH5alpha strain (Hanahan, 1983) was the host for the *Sac. erythraea* genome fragment library. Plasmid pIJ487 (Ward et al., 1986) was provided by Mervyn Bibb, John Innes Centre, Norwich, England. and pBS(+) was purchased from Stratagene, Inc. (LaJolla, Calif.).

Chemicals and Biochemical Reagents

Erythromycin A (Em), tetrazolium chloride, was obtained from Sigma. Thiostrepton (Ts) was provided by S. J. Lucania (Bristol Meyers Squibb, N.J.).

Media and handling

E20A agar medium (Weber and McAlpine, 1991) contains, per 1 liter aqueous solution: 5 g bacto-soytone, 5 g soluble starch, 3 g $CaCO_3$, 2.1 g MOPS buffer, and 20 g bacto-agar. E20A agar containing 50 µg/ml of thiostrepton (E20A-Ts50) was used when selection for thiostrepton-resistance ($Ts^R$) was required for maintenance of plasmids or induction of the Blu phenotype in *S. lividans*. Carbon sources other than starch were sometimes used, and were added at 5 g/L. Substitution of peptone for soytone, was also done using equal weights. E29F broth medium (Weber and McAlpine, 1991), which contains per 1 liter: 22 g nutrisoy flour (ADM); 15 g soluble starch (Difco); 3 g $CaCO_3$ (J. T. Baker); 0.5 g $MgSO_4$-$7H_2O$; 0.015 g $FeSO_4$.$7H_2O$, and 50 ml soybean oil. R2T2 regeneration plates (Weber et al., 1989; Weber et al., 1985) were used for the selection of transformants using both *Sac. erythraea* and *S. lividans* host strains. Tryptic Soy Broth (TSB, Difco Laboratories, Detroit, Mich.), prepared according to manufacturers recommendations.

Fermentation protocol for the production of erythromycin by *Sac. erythraea* in shake flasks Spores of *Sac. erythraea* were transferred asceptically from a slant or plate culture to 4 ml of sterile TSB broth in duplicate 16×125 mm capped test tubes. Spore inocula of all experimental and control cultures was prepared in advance to be less than two weeks old. Test tube cultures were grown in a shaker for 2 days at 32° C. at a slight angle from vertical. The contents of one tube were mixed with the duplicate tube. A 3 ml portion of the mixture was transferred to 30 ml of regular or modified E29F medium. Weights were recorded of flasks after inoculation; the cultures were grown in 250 ml non-baffled shake flasks for 5 days at 32° C., 400 rpm (one inch rotary displacement). After 5 days, the color of the culture was recorded and the flasks were re-weighed and adjusted to their original weight through the addition of sterile water to compensate for water lost due to evaporation. The cultures were also streaked onto R2T2 to check for contamination. Cells were then pelleted by centrifugation and the broth was decanted into 50 ml plastic Corning tubes for storage at 4° C. until they were bioassayed.

Bioassay for erythromycin

A large plate (Coming Costar, Cambridge, Mass., 245 mm square bioassay dish, (cat. no. 431111), double-agar layer system was used. The bottom agar layer consisted of 100 ml TSB agar. Once solidified (sitting 1 hour at room temperature) a top agar layer was poured. Top agar consisted of 100 ml TSB agar containing 200 µl 1% tetrazolium red (Sigma) and a sufficient quantity of *B. subtilis* thiostreption-resistant spores to produce a confluent lawn of growth. The upper layer was solidified at room temperature for 1 hour with the lid slightly open, or the plate was placed open in a laminar flow hood to remove any moisture from the surface of the plate. Broth samples (10 µl) were spotted onto ¼ inch bioassay discs (Schleicher and Schuell, Keene, N.H.) and dried for 30 min. Standard erythromycin A solutions were prepared at 5, 10, 25, 50, 100, and 250 µg/ml and used to wet bioassay discs which were dried and stored at room temperature and placed onto the plate at the time the dried experimental samples were applied. The bioassay plate was incubated overnight at 37° C. Following incubation, the zones were measured, and converted to concentrations using the standard curve produced for each plate.

EXAMPLE 2

Preparation of pFL37

A. Construction of cloning vector pFL8

Plasmid pFL8 was constructed for this study to serve as the cloning vector for the library of *Sac. erythraea* DNA fragments in both *E. coli* and *S. lividans*. Details of its construction are described by Hessler et al, 1997. Plasmid pFL8 and its deriviatives including pFL37 (FIG. 1) are maintained as a high-copy autonomously replicating plasmid in *S. lividans* and has the properties and functions of pIJ487 (Ward et al., 1986) including the pIJ101 origin of replication, the thiostrepton resistance gene (tsr), and the promoterless kanamycin reporter gene (neo) from Tn5 (Beck et al., 1982). A feature of pFL8 and deriviatives that is unique to the *Sac. erythraea* cloning vectors reported thus far (Weber and Losick, 1988; Vara et al., 1989; Weber et al., 1990) is the placement of the promoterless neo gene proximal to the pBS(+) multiple cloning site. This arrangement allows for blue/white X-gal dependant screening of clones in *E. coli* and the subsequent activation of neo expression in *S. lividans* and *Sac. erythraea* by promoters which may be contained on the cloned fragment. Selection for higher levels of kanamycin resistance in integrated transformants of *Sac. erythraea* leads to the amplification of the plasmid including the cloned sequences in the *Sac. erythraea* genome (described below).

B. Construction of *Sac. erythraea* DNA library in *S. lividans*

Two to five kb Sau3A fragments from *Sac. erythraea* ATCC 11635 were produced by partial Sau3A digestion of genomic DNA followed by preparative agarose gel electrophoresis and extraction of the properly sized DNA from the gel. The mixture of Sau3A DNA fragments was ligated to BamHI-digested pFL8 and transformed by electroporation into *E. coli* DH5alpha. Transformants were selected on LB plates containing X-gal and 100 μg/m ampicillin, and 7,200 white transformants (those containing inserts) were picked to duplicate grid plates containing 50 colonies per plate. One plate from each pair of grid plates was scraped, and the cells from 12 plates (600 colonies) were combined into a sublibrary. Cell preps from the 12 sublibraries were kept separate for the isolation of plasmid DNA. The plasmid DNA from the 12 groups was then transformed into *S. lividans* in separate transformation experiments.

DNA from the *E. coli* sub-libraries was transformed in separate reactions into protoplasts of *S. lividans* TK21. Thiostrepton resistant colonies appearing on the primary transformation plates (R2T2 agar containing 50, μg/ml of Ts) were visually screened for pigment production and other morphological and sporulation-related phenotypes. Because the R2T2 regeneration medium is not favorable for actinorhodin production or sporulation of *S. lividans*, the colonies were transferred (still on the agar), to an E20A (U.S. Pat. No. 5,141,926) agar plate containing 50, μg/ml of Ts. This stimulated sporulation and pigment formation by the colonies. The spores of primary transformants were harvested and replated at single-colony densities on different screening media, usually E20A containing 50 μg/ml of Ts or Complete medium (Hopwood et al., 1985). Over 50,000 colonies were visually screened for pigmented mutants. Since red variants of *S. lividans* occurred spontaneously at high frequency we limited our screen to blue or gray pigmented colonies.

Eleven *S. lividans* transformants with blue or altered pigmentation (Blu phenotype) were found from the visual screening on E20A-Ts50 plates. For pFL37 transformants (FIG. 1) it was observed that thiostrepton in the media was required for the stimulation of blue pigment production. Very low levels of thiostrepton (less than or equal to 100 ng/ml) were sufficient to induce Blu. Besides stimulating blue pigment formation, plasmid pFL37 also appeared to stimulate the formation of more highly confluent and darker grey spores in the *S. lividans* host when compared to the parent strain. pFL37 was stable, for example, when plasmid DNA was isolated from an *S. lividans* transformant carrying pFL37 and passaged through *E. coli* then returned to *S. lividans*, nearly all of the re-transformants in *S. lividans* turned blue.

When starch was not included in the E20A-Ts50 agar medium or if it was substituted with a different carbon source, pFL37 transformants grew normally but completely lost the ability to make blue pigment. The Blu phenotype was restored when the cells were transferred back to a medium containing thiostrepton and starch. The Blu phenotype was not even weakly observed using any other carbon source besides starch (or the starch derived malto-dextrin), including sucrose, glucose, alpha or beta-lactose, mannose, L-sorbose, or maltose. If starch was included in the media with any of the other carbon sources, the strain regained its ability to make blue pigment.

Investigation of the effects of nitrogen source revealed that casein-derived peptone could be substituted for soytone in the E20A-Ts50 agar with no substantial effect on blue pigment formation for pFL37 transformants.

C. DNA sequencing

Plasmid templates pFL205, pFL206, pFL207, and pFL37 were purified by Qiagen preparation procedure and submitted for automated sequencing using the ABI model 377 instrument at the Iowa State University Nucleic Acid Facility (Ames, Iowa).

D. Subcloning of pFL37

(i) construction of pFL186, pFL184

Plasmid pFL37 was digested to completion with KpnI and BamHI, producing five fragments. One 2.25 kb KpnI fragment covering the left half of clone 37, and a second 2.4 Kb BamHI-KpnI fragment covering the right-half of the insert were purified from agarose gels by Gene Clean™ (Bio101, Vista, Calif.) and subcloned into pBS(+) with complementary ends to create subclones pFL176 and pFL175, respectively. These two fragments were subsequently subcloned following EcoRI and HindIII double digestion into the complementary sites in pFL8 to create pFL186 and pFL184.

(ii) Construction of pFL211, pFL212, pFL213, and pFL216

Figure 2:
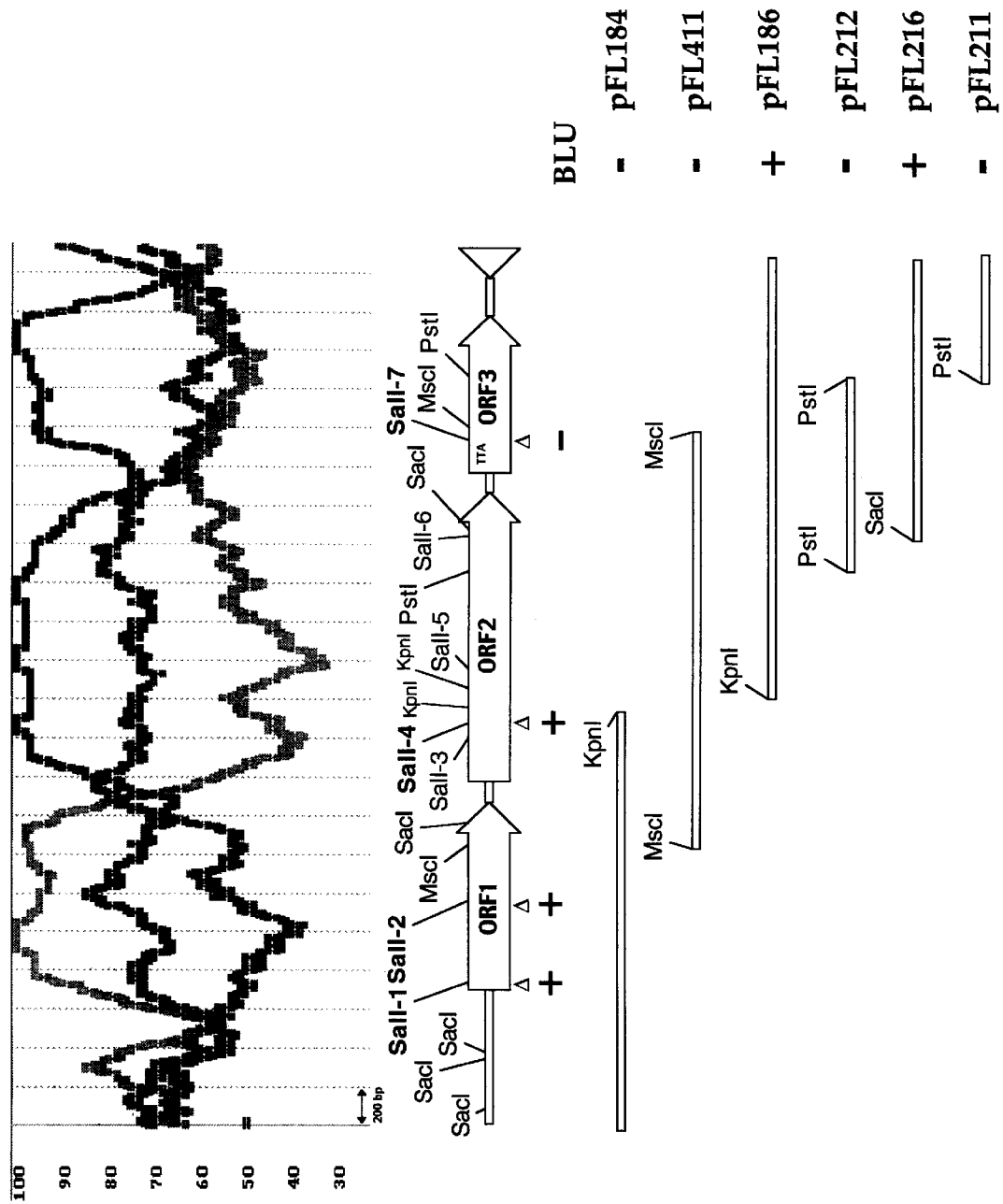
FIG. 2 shows the FRAME analysis of the cloned fragment contained in pFL37. Arrows below the plot indicate size and direction of the ORFs identified. TTA in the ORF3 open arrow indicates the location of the rare TTA codon in ORF3. Shown below the FRAME plot is the subcloning and insertional mutagenesis of clone 37. Subcloning: Open bars with no arrow heads below the ORF map represent the subclones of the original 4.8 kb fragment that were tested for their ability to stimulate blue pigment production in *S. lividans* when carried on plasmid pFL8. Two subclones, pFL186 and pFL216 were able to stimulate Blu equally as well as the parent clone (indicated by "+" symbols to right). Insertional inactivation: darts pointing to ORF map indicate the SalI sites of insertion of the aphAl (Km-resistance) gene that was inserted as a SalI cassette isolated originally from pUC4K (Pharmacia LKB Biotech); insertions are numbered for reference above the darts. "+", blue pigment formation; "−" no blue pigment formation.

Plasmid pFL216 was digested with SacI and religated, which removed a 870 bp SacI fragment from the left side of the insert in pFL186; the resultant plasmid was called pFL37LS. The 870 bp SacI fragment deleted from pFL186 was then ligated to SacI digested pBS(+) and the resultant plasmid was designated pFL207. In another experiment, plasmid pFL186 was digested to completion with PstI spliting the insert into three fragments (FIG. 2). Two of these fragments were subcloned into PstI digested pBS(+) to form pFL205 and pFL206. Each of these plasmids was then cut with HindIII and EcoRI to remove the inserts which were then ligated to HindIII and EcoRI digested pFL8, the resulting plasmids were called pFL212 and pFL211.

E. In vitro insertional mutagenesis of the insert in pFL37

The parent plasmid pFL37 was partially digested with SalI and the singly-cut, linearized form was purified from an agarose gel using Gene Clean™. This band containing a mixture of different linearized forms of pFL37 was then ligated to the SalI fragment from pUC4K (Pharmacia LKB Biotechnology, Piscataway, N.J.) containing the aphA1 gene from Tn903 which confers kanamycin resistance (KmR). The ligation reaction was transformed into *E. coli* DH5alpha and transformants were selected on LB-Km50 plates. Plasmids from $Km^R$ transformants were subjected to restriction analysis to determine the site and orientation of the aphA1 gene in the plasmid. The ligation resulted a library of plasmids with the aphA1 gene inserted into the various SalI sites in pFL37. Two insertions were made into ORF1 and one insertion was made into each of the other two ORFs (FIG. 2).

F. DNA Sequence analysis of the pFL37 insert

Three complete colinear open reading frames (ORFs) were found from DNA sequence analysis (FIG. 2). These ORFs were bounded at their 3' end by one incomplete convergent ORF, ORF4, and on the 5' end by a 732 bp untranslated region not containing any readily apparent ORFs. The ORF assignments were made based on codon bias using the program FRAME (Kleman et al., 1993), putative ribosome binding sites located upstream of AUG or GUG start codons, and by comparative analysis to homolgous genes using the BLAST program. BLAST homology searches were also helpful in providing insight into the functions of the genes found on pFL37 described below.

ORF1 (1026 bp) showed a 38% overall identity to a repressor protein from the well characterized LacI-GalR family (Weickert and Adhya, 1992, Bussey and Switzer, 1993). This family of repressors are known to coordinate the utilization and transport of carbohydrates in a wide variety of Gram-positive and Gram-negative organisms. The highest homology for ORF1 was to hypothetical proteins from *S. ambofaciens* and *S. lividans*. These previously described LacI homologs from *Streptomyces* have been found to be large repeated sequences associated with amplifiable units of DNA (Piendl et al., 1994, Volff et al., 1996). The LacI homolog of *Sac. erythraea* appears to be present in only one copy in the chromosome based on Southern hybridization analysis.

Recently a report of the cloning and characterization of a new LacI homolog from *S. coelicolor* has appeared (van Wezel et al., 1997). The ORF1 described here clearly shares a much higher degree of homology to the *S. lividans* and *S. ambofaciens* AUD gene family than with the new gene from *S. coelicolor*.

Using the BLAST program, ORF2 showed exceptionally high homology to the *T. curvata* alpha-glucosidase gene. The homology of the deduced amino acid sequence of ORF2to the *T. curvata* protein (unpublished, GenBank Accession Number U17917) also showed high homology. The amino acid identities were in the range of 60–70% over the major portion of the protein. The other highly homologous proteins based on BLAST results included an oligo-1, 6-glucosidase from *Bacillus thermoglucosidasius* (Watanabe et al., 1991) and trehalose-6-phosphate hydrolase from *E. coli*.

The function of the smallest ORF, ORF3 (852 bp), could not be deduced from BLAST homology searches. Perhaps of significance to the function of ORF3 is the appearance and location of a predicted UUA (leucine) codon at position 7 FIG. 4A–FIG. 4I. This is the only UUA codon in clone 37. In related Actinomycetes, the UUA codon is also found only rarely, and is associated so far only with a few genes (most noteably, actII-ORF4) that fall into a class of bldA-dependent regulatory genes. It has been suggested that the bldA-like mechanism, acting through the rare UUA codon in selected regulatory genes, may be a general type of control mechanism in Actinomycetes McCue et al., 1992; Geistlich et al., 1992). At the right end of clone 37 (FIG. 2), a short portion of the C-terminus of a convergent ORF, designated ORF4, was found. Blast results indicated that this gene was most likely involved in nitrogen metabolism.

This loop sequence of unknown function contains a shorter repeated pentanucleotide sequence, TTTCC, which appears five times within the 172 bp region, and no where else in the cloned DNA sequence. Further downstream other motifs are evident; three regions containing sequence symetries (412–447 bp; 579–595 bp, and 598–607 bp). Also, a large (14/16 bp) direct repeat is also in this region. In summary, based on analysis of the DNA sequence, clone 37 contains two genes involved in carbohydrate utilization and one new type of gene, possibly a regulatory gene based on data presented below.

G. Subcloning of the DNA fragment from pFL37 responsible for Blu

Subcloning experiments revealed the region of clone 37 responsible for the Blu phenotype (FIG. 2). In the first subcloning experiment, each half of the 4.7 kb insert was tested and only the 2.3 kb right-side fragment (subclone in pFL186, FIG. 2) produced Blu transformants. PFL186 was further trimmed from the left, leaving a 1.47 kb fragment, that was still capable of inducing Blu on plasmid pFL216. Any further subcloning (pFL211 and pFL212) resulted in the loss of Blu production. Blu, therefore, was conferred minimally by sequences from within the 1.47 kb right end of clone 37, carried on plasmid pFL216. It was later determined through DNA sequencing analysis (below) that the insert in pFL216 contained one complete open reading frame, originally designated as ORF3 and now given the designation eroA for "erythromycin regulatory ORF".

EXAMPLE 3

Transformation Studies

A. Protoplast preparation and integrative transformation of *Sac. Erythraea* 11635

A modified version of the PEG-mediated protoplast protocol described by Weber and Losick (1988) was used.

B. Production of integrated transformants

Primary transformants were incubated long enough to produce fully mature spores on the R2T2 regeneration plates; usually this took one week at 32° C. The spores were then harvested, separated from the mycelial fragments, and plated directly at high density on fresh R2T2 plates containing 10 µg/ml of thiostrepton. Only spores that contained integrated plasmids germinated and grew into normal colonies on this plate. Plasmids with larger inserts (i.e. larger regions of homology) produced greater numbers of thiostrepton-resistant spores at this stage. Integrations were achieved with inserts as small as 360 bp.

C. Gene replacement in *Sac. erythraea*

Integrated transformants that were used for gene replacement carried both the Ts-resistance gene on the plasmid and the Km-resistance gene inserted into the gene of interest. Spores of the integrated transformants were passed nonselectively through a cycle of growth and sporulation, allowing for spontaneous excision of the integrated vector. Excision of the plasmid produced candidate strains that were thiostrepton sensitive and depending on the site of the second crossover would be either Km-resistant or Km-sensitive. Km-resistant strains were desired because they would be carrying the Km gene insertion into the gene of interest. Chromosomal Southern analysis of the excised transformant derivatives was used to physically identify the strains in which gene replacement had occurred.

D. Amplification of integrated plasmids in *Sac. erythraea*

Integrated transformants with pFL37 were resistant to 20 µg/ml of kanamycin on E20A agar plates. To isolate more highly resistant varients of the integrated strain, a dense spore suspension was plated on E20A plates with 50 µg/ml of kanamycin. Single colonies appeared that were then restreaked on the same medium. The mycelia harvested from these plates were then transferred at high density to E20A containing kanamycin at 1000 µg/ml. Single colonies appeared that were then streaked onto the same medium, which was then used as the inoculum for erythromycin fermentations.

E. Southern Analysis

Southern blots were produced using the method described in Sambrooke et al., (1989). Hybridization and detection materials and methods used are described in the Supersignal™ Chemiluminescent Substrate Kit available from Pierce Chemicals, (Rockford, Ill.).

F. Insertional inactivation of ORFs in pFL37: effects in *S. lividans*

Once the plasmid had been sequenced and the ORFs delineated, mutations were targeted to the three ORFs to determine their effect on the Blu phenotype in *S. lividans* (FIG. 2). Insertional inactivation experiments were performed with the aphA1 (kanamycin resistance) gene cartridge from pUC4K (Pharmacia) as the selectable insertion marker. Insertion of aphA1 into two different SalI sites in ORF1 or into the 5' proximal SalI site of ORF2 did not affect the Blu phenotype. Insertion of aphA1 into the unique SalI site of eroA (ORF3), however, caused the complete loss of blue pigment formation and gray spore formation. These results were readily consistant with the conclusions drawn from the subcloning analyses indicating that only the fragment containing eroA, (ORF3), was required for the Blu phenotype and gray spores (FIG. 2). ps G. Transformation and amplification of pFL37 in *Sac. erythraea* stimulation of erythromycin production Transformants of the red varient strain of *Sac. erythraea* with pFL37 were significantly better producers of erythromycin than the original red strain. Fermentations of amplified transformants of *Sac erythraea* with pFL37 in modified E29F media showed 65% higher Em-production over the parent strain (FIG. 3A, experiment 1). In this experiment the red strain produced 0.060 g/L of erythromycin in the modified E29F media, while the pFL37 transformant grown under the same conditions, produced 0.110 g/ml. In a second series of experiments using another type of modified E29F medium without oil, similar increases were obtained by the transformed and amplified strains (FIG. 3A, experiments 2–4) The increases shown by the transformed red varient strain varied between 68% to 147% above the level of production of the untransformed strain. The Em yield increase was obtained without the need to place selective pressure on the plasmid by adding thiostrepton to the fermentation media. Southern analysis of the chromosome showed that the plasmid was stable and remained amplified under these non-selective conditions. In the event that the strain was used commercially, it would be impractical to consider adding a drug like thiostrepton to the media, fortunately our experiments showed that this would not be necessary.

To address the question of whether pFL37 would have a proportionate positive effect in a substantially higher-yielding strain, the plasmid was transformed into the white variant of *Sac. erythraea* ATCC11635 which makes approximately 5 times more erythromycin than the red variant. The results (FIG. 3B) showed that the yield increase was proportionately the same in the white strain as it was in the red strain. The yields from three shake flasks of the untransformed "white" strain averaged 0.415 g/L; following transformation, and without amplification, the yield jumped up to 0.687 g/L, an increase of 65%.

H. Inactivation of ORF2 causes a marked reduction in erythromycin production

A targeted gene replacement strategy was utilized to insertionally inactivate ORF2 and ORF3 with the aphA1 gene from Tn903 (FIG. 2). Insertions into the ORF2 locus caused an 80% reduction in erythromycin production. Insertions into the ero A (ORF3) only a caused a slight reduction. Inactivation of ORF1 in *Sac. erythraea* appears to have no effect.

Experiments were also done in *Sac. erythraea* to determine whether a requirement for thiostrepton or starch existed for the stimulation of erythromycin production as it had in *S. lividans* for the stimulation of blue pigment formation. The stimulation of erythromycin production occurred regardless of whether thiostrepton or starch were added to the growth medium. Other carbon sources such as glucose, sucrose, and maltose could substitute for starch with no negative effect on erythromycin production by either the transformed or the untransformed strains. These results taken with the result that the knockout of ORF2 had an effect on erythromycin production but not blue pigment formation indicate that pFL37 may act differently in the two hosts to stimulate secondary metabolite production.

Aubert, M., E. Weber, D. Schneider, J. M. Simonet, and B. Decaris. 1993. Primary structure analysis of a duplicated region in the amplifiable AUD6 locus of *Streptomyces ambofaciens* DSM 40697. FEMS *Microbiol Lett* 113: 49–56.

Beck, E, G. Ludwig, E. A. Auerswald, B. Reiss, H. Schaller (1982). Nucleotide sequence and exact localization of the neomycin phosphotransferase gene from transposon Tn5. *Gene* 19:327–336.

Bunch and McGuire (1953). Erythromycin, its salts, and method of preparation. U.S. Pat. No. 2,653,899.

Bussey, L. B., and R. L. Switzer. 1993. The degA gene product accelerates degradation of *Bacillus subtilis* phosphoribosylpyrophosphate amidotransferase in *Escherichia coli*. *J Bacteriol.* 175:6348–6353.

Chater, K. F. and M. J. Bibb. (1997). Regulation of bacterial antibiotic production. Biotechnology Vol. 6: Products of Secondary Metabolism. Eds. H. Kleinkauf and H. von Dohren; VCH, Weinheim, Germany (in press).

Fernandez-Moreno, M. A., A. J. Martin-Triana, E. Martinez, J. Niemi, H. M. Kieser, D. A. Hopwood, and F. Malpartida. (1992). abaA, a new pleiotropic regulatory locus for antibiotic production in *Streptomyces coelicolor*. *J. Bacteriol.* 174: 2958–2967.

Geistlich, M., R. Losick, J. R. Turner, R. N. Rao. 1992. Characterization of a novel regulatory gene governing the expression of a polyketide synthase gene in *Streptomyces ambofaciens*. *Mol. Microbiol.* 6: 2019–2029.

Hanahan, D. 1983. Studied on transformation of *Escherichia coli* with plasmids. *J. Mol. Biol.* 166: 557–580.

Hopwood, D. A., M. J. Bibb, K. F. Chater, T. Kieser, C. J. Bruton, H. M. Kieser, D. J. Lydiate, C. P. Smith, J. M. Ward, and H. Schrempf. 1985. Genetic manipulations of Streptomyces, a laboratory manual. John Innes Foundation, Norwich, England.

Horinouchi, S., O. Hara, and T. Beppu. 1983. Cloning of a pleiotropic gene that positively controls biosynthesis of A-factor, actinorhodin, and prodigiosin in *Streptomyces coelicolor* A3(2) and *Streptomyces lividans*. *J Bacteriol.* 155, 1238–1248.

Horinouchi, S. and T. Beppu. 1984. Production in Large Quantities of Actinorhodin and Undecylprodigiosin Induced by afsB in *Streptomyces lividans*. *Agric. Biol. Chem.* 48, 2131–2133.

Ishizuka, H., S. Horinouchi, H. M. Kieser, D. A. Hopwood, and T. Beppu. (1992). A putative two-component regulatory system involved in secondary metabolism in Streptomyces spp. *J Bacteriol.* 174:7585–7594.

Kleman, G. L., W. R. Strohl 1993, ftp. Bio. Indrana. Edu (129.79, 224–25)/Mol Biol/Ibmpc/Frame.Zip.PC Programs for FRAME and Codon Preference Analysis.

McCue, L. A., J. Kwak, M. J. Babcock, and K. E. Kendrick. (1992). Molecular analysis of sporulation in *Streptomyces griseus*. *Gene* 115:173–179.

Murakami, T., T. G. Holt and C. J. Thompson. 1989. Thiostrepton-induced gene expression in *Streptomyces lividans*. J. Bacteriol. 171, 1459–1466.

Piendl, W., C. Eichenseer, P. Viel, J. Altenbuchner, and J. Cullum. 1994. Analysis of putative DNA amplification genes in the element AUDI of *Streptomyces lividans* 66. *Mol Gen Genet* 244:439–443.

Queener, S. W. and D. H. Lively. 1986. Screening and selection for strain improvement, p 155–169. In Manual of Industrial Microbiology and Biotechnology. Eds. A. L. Demain and N. A. Solomon. American Society for Microbiology, Washington D.C.

Romero, N. M., V. Parro, F. Malpartida, and R. P. Mellado. 1992. Heterologous activation of the actinorhodin biosynthetic pathway in *Streptomyces lividans*. *Nucleic Acids Res.* 20: 2767–2772.

Sambrook, J., E. F. Fritsch, and T. Maniatis. 1989. Molecular Cloning: A laboratory manual. Cold Spring Harbor Laboratory, Cold Spring Harbor, N.Y.

van Wezel, G. P., J. White, P. Young, P. W. Postma, and M. J. Bibb. 1997. Substrate induction and glucose repression of maltose utilization by *Streptomyces coelicolor* A3(2) is controlled by malR, a member of the lacI-galR family of regulatory genes. *Mol. Microbiol* 23: xxxx-xxxx.

Vara, J. M. Lewandowska-Skarbek, Y. G. Wang, S. Donadio, C. R. Hutchinson. 1989. Cloning of genes governing the deoxy sugar portion of the erythromycin biosynthesis pathway in *Saccharopolyspora erythraea* (*Streptomyces erythreus*) J. Bacteriol.,171: 5872–5881.

Volff, J.-N., C. Eichenseer, P. Viell, W. Piendl, and J. Altenbuchner (1996). Nucleotide sequence and role in DNA amplification of the direct repeats composing the amplifiable element AUD1 of *Streptomyces lividans* 66. *Mol. Microbiol* 21: 1037–1047.

Watanabe, K., Chishiro, K., Kitamura, K. and Suzuki, Y. (1991) Proline residues responsible for thermostability occur with high frequency in the loop regions of an extremely thermostable oligo-1,6-glucosidase from *Bacillus thermoglucosidasius* KP1006 *J. Biol. Chem.* 266, 24287–24294 (1991)

Ward, J. M., G. R. Janssen, T. Kieser, M. J. Bibb, M. J. Buttner, and M. J. Bibb. 1986. Construction and characterization of a series of multi-copy promoter-probe plasmid vectors for Streptomyces using the aminoglycoside phosphotransferase gene from Tn5 as indicator. *Mol. Gen. Genet.* 203:468–478.

Weber, J. M., J. O. Leung, G. T. Maine, R H. B. Potenz, T. J. Paulus and J. P. DeWitt. 1990. Organization of a cluster of erythromycin genes in *Saccharopolyspora erythraea*. *J. Bacteriol.* 172, 2372–2383.

Weber, J. M. and R. Losick. 1988. The use of a chromosome integration vector to map erythromycin resistance and production genes in *Saccharopolyspora erythraea* (*Streptomyces erythraeus*). *Gene* 68, 173–180.

Weber, J. M., B. Schoner, and R. Losick. 1989. Identification of a gene required for the terminal step in erythromycin biosynthesis in *Saccharopolyspora erythraea* (*Streptomyces erythraeus*). *Gene* 75, 235–241.

Weber, J. M., C. K. Wierman, and C. R. Hutchinson. 1985. Genetic analysis of erythromycin production in *Streptomyces erythraeus*. *J. Bacteriol.* 164, 425–433.

Weickert, M. J., and S. Adhya. 1992. A family of bacterial regulators homologous to Gal and Lac repressors. *J. Biol. Chem.* 267:15869–15874.

Weber, J. M. and J. B. McAlpine. 1991. Erythromycin Derivatives. U.S. Pat. No. 5,141,926.

---

What is claimed is:

1. An isolated and purified polynucleotide comprising:
   (a) the nucleotide sequence of SEQ ID NO:1 from nucleotide number 733 to nucleotide number 1758, the nucleotide sequence of SEQ ID NO:1 from nucleotide number 1899 to nucleotide number 3451, or the nucleotide sequence of SEQ ID NO:1 from nucleotide number 3560 to nucleotide number 4411:
   (b) sequences that are complementary to the sequence of (a); or
   (c) sequences which encode the polypeptides of SEQ ID NO; 2, 3 or 4.

2. The polynucleotide of claim 1 that is a DNA molecule.

3. The polynucleotide of claim 1 is an RNA molecule.

4. The polynucleotide of claim 1 having the nucleotide sequence of SEQ ID NO:1 from nucleotide number 733 to nucleotide number 3451.

5. The polynucleotide of claim 1 having the nucleotide sequence of SEQ ID NO:1 from nucleotide number 733 to nucleotide number 4411.

6. The polypeptide of claim 1 that contains both the nucleotide sequence of SEQ ID NO:1 from nucleotide number 733 to nucleotide number 1758 and the nucleotide sequence of SEQ ID NO:1 from nucleotide number 1889 to nucleotide number 3451.

7. The polynucleotide of claim 1 that contains both the nucleotide sequence of SEQ ID NO:1 from nucleotide number 733 to nucleotide number 1758 and the nucleotide sequence of SEQ ID NO:1 from nucleotide number 3560 to nucleotide number 4411.

8. The polynucleotide of claim 1 that contains both the nucleotide sequence of SEQ ID NO:1 from nucleotide number 1899 to nucleotide number 3451 and the nucleotide sequence of SEQ ID NO:1 from nucleotide number 3560 to nucleotide number 4411.

9. The polynucleotide of claim 1 that contains the nucleotide sequence of SEQ ID NO:1 from nucleotide number 733 to nucleotide number 1758, the nucleotide sequence of SEQ ID NO:1 from nucleotide number 1889 to nucleotide number 3451, and the nucleotide sequence of SEQ ID NO:1 from nucleotide number 3560 to nucleotide number 4411.

10. The polynucleotide of claim 1 having the nucleotide sequence of SEQ ID NO:1.

11. An expression vector comprising the polynucleotide of claim 1 wherein the expression vector drives expression of the polynucleotide in a cell.

12. The expression vector of claim 11 wherein the polynucleotide sequence of SEQ ID NO:1 from nucleotide number 733 to nucleotide number 4411.

13. A host cell transformed with the polynucleotide of claim 1.

14. The host cell of claim 13 wherein the polynucleotide has the nucleotide sequence of SEQ ID NO:1 from nucleotide number 733 to nucleotide number 4411.

15. The host cell of claim 13 that is a bacterial cell.

16. The host cell of claim 15 that is an Actinomycete.

17. The host cell of claim 16 that is a *Sac. erythraea*.

18. The host cell of claim 13 wherein the polynucleotide has the nucleotide sequence of SEQ ID NO:1 from nucleotide number 733 to nucleotide number 4411.

19. A process of making polypeptides that enhance erythromycin production comprising transforming a suitable host cell with the expression vector of claim 12 and maintaining the transformed cell under conditions and for a period of time sufficient for production of the polypeptide.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 4776 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:1:

```
GGATCATCTC CCAGATTTCT CCCACGGCAC CGGGGATGCC AACCGGCGCG CCGTCTCGCC      60

CCGGCGGTTC GGGTCGGAAG TCAAGAGCTC GGAAACCCGC CTTCGTCGTC ACCGCTGGCC     120

GCTCTCGCAC GCGCGTGCCA CGCGCGCGCG AGGCGACTGC GTTTCCCAAG GTCGGAGTTC     180

CGAGGTGCTA CCCGATTTCC GACCCAGTTT CCGAGAGGCG CGCTCATGGC CGGCGCATGC     240

ACAGCGGGCC GGGGGTCACG CTTCGTGTTC CCTACTCGTT TCCCTACTCG GTCTCCCTGA     300

CGCCCTTTCC AGATGCGCCT ACGCGCGCGC CCGCGCGCGT GACGGTTGGC GCCCGCTCGA     360

GCTCCCCGCC CACGAATCCC GATCTCGGCG AACACCGAGC TCTCCGACGG GTTGCTGGTG     420

TCCCAGTAGA CGACGCGGTC GGCGTTGCCC GCGCCCGAGC CGCACGCGGT GAGTGCGAGC     480

GCGCTGACCA GGCCGAGTGC GGCGACGGTG GCGGTGGCCT TGGGTCTCAT GAGGCGGTGT     540
```

```
CCTCCCAGCT TTGCAAAAAC TTGCGAGTAC CTGGCCGTAA ATTGCATACC CGAAACGTGA      600

GAAGAGTCAA GGTTTTTCGG ATGTTCACCG AACGAGCGCG CCGGTCGTGT CAGGTCAACG      660

TTTGCAAAAC ATTGCGCAAC CGTGCAGGAT TGTGGGCGCA ACACCGCCGT CGGCGAGGAG      720

GATCGATCTG AAGTGGCGGG TCTGTCGGAT ATCGCCAAGG CTGCCGGAGT CAGCGTGTCG      780

ACGGTCAGCC GGGTGCTCAA CCGCCGGGCG GGCATCAAGG AGGACACCCG CCAGCGCGTG      840

CTGGCCGTGC TCAACGAGAT GCCGCACACC GCGCGCGGCA TAGGTGCGCT GCGCCGCACC      900

GGGGTAATCG GCCTGCTGGT GCCGGAGCTG TCCAACCCGG TGTTCCCGGC CTTCGCCGAG      960

GCCCTGGAGG CGCGCGCGGT CGGCGCGGGC TACGCCTCGC TGCTGTGCAA CACCCGCGTC     1020

GGGATGAGCG AGGAGGACTA CGTCCGGATG CTCATCGCCC GCGGCGTGGA GGGCATGGTC     1080

TTCGTGTCGC CGGAGATCGC CAACACCGAG GGCGAGCAGC GGATCAGCCG CAGCTACTAC     1140

GAGAAGCTGC TGGCCGACGG CGTGCGCATG GTCTTCGTCA ACGGCGGCGC GCCGACGCTG     1200

GACGTGCCCG ACGTCGCCGT CGACGAGCAC CTGGCCGGCT ACACCGCCAC CCGCCACCTG     1260

CTCGACCTCG GCACCGGCG GATCGGTTTC GTCAGCGGTC CCGCCCGCGC GGTGCCCTCG     1320

CGGCTCAAGC GCGCAGGCTG GGCCGCTGCG CTGGAGGAGG CCGACATCGC CCCGGACCCG     1380

CGGCTGGTCG CGCACGCGCC GTTCGGCGCG GAGGGCGGCG CGCAGGCCAT GGCCGAGCTG     1440

CTCGAAACCG CGGGCCCCAC CGCCGTGATG TGCTCGTCGG ACGTCATGGC GCTCGGCGCG     1500

ATGCGCGAGG CCAAGCGGCG CGGACTGGCC ACCCCGGAGG ACCTGTCGGT GGTCGGCTTC     1560

GACGACATCG CGCTGGCCTC CTACTGCCAG CCGGCGCTGA CGACGCTGGC GCAGCCGATC     1620

GAGGAGATGG CCGCCGCGGC GGTGGACGAG CTCTCCCGCC GCCTCGACCC GGACCAGCCG     1680

GGCCGCGCGA CGACGAGCTT CAGCCGGATG TTCCGCCCGA ACCTGGTGGT GCGGGAGTCC     1740

ACCGCCGCCC CGCGCTGACC GCGGCGGCGG CGAATCGCTT GCAGGAGAAG TCGGAGTTCC     1800

GGCCTCCACG CGCGTGCGCG CGGCCGGAGC GCCACCGCCA CATCGGCGGG AACCGTGGGA     1860

AGGGGTACTG GTGCTCAGGG GTGCGGGAGT GCGCGGAACG GCCGCCGACT GGTGGCGCGA     1920

CGCGGTGGTG TACCAGGTCT ACGTCCGCAG CTTCGCCGAC GCCGACGGCG ACGGGATCGG     1980

CGACCTGGCG GGCGTGCGCG CAAGGCTGCC GTACCTGGTG GAGCTGGGTG TGGACGCGGT     2040

CTGGCTCACG CCGTTCTACC CGTCGCCGAT GGCCGACGGC GGCTACGACG TCGCCGACTA     2100

CTGCGACGTC GACCCGATGT TCGGCACGCT CGACGACTTC GACGACCTGC TGGCGCGGGC     2160

GCACTCGCTG GGCCTGAAGG TGATCGTCGA CGTCGTGCCC AACCACACCT CCGACGCGCA     2220

CCCGTGGTTC GCCGAGGCGC TGGAGGCCGG GCCGGGCGAC CCGGCGCGGG AGCGGTACCT     2280

GTTCCGCGAC GGGCGCGGCG AGAGCGGGGA GCTGCCGCCC AACGACTGGG AGTCATCCTT     2340

CGGCGGTCCG GCGTGGACCC GCGTCCCCGA CGGCCAGTGG TACCTGCACC TGTTCGCCCC     2400

CGAGCAGCCC GACCTGAACT GGCGCAACCC GCAGATCCGC GCGGAGTTCG CCAAGGTGCT     2460

GGAGTTCTGG CTGGACCGCG GGGTCGACGG CTTCCGGATC GACGTCGCCC ACGGCATGAT     2520

CAAGCACCCC GACCTGCCCG ACACCGGGCT GCACCAGCAG ATCTCCCTGC TCGGCCGGGC     2580

CGAGCTGCCC TACTTCGACC AGGACGAGGT GCACGGCATC TACCGGGAGT GGCGCGAGCT     2640

GCTGGACTCC TACGAGGGCG CCCGGATCGG GGTGGCCGAG GCGTGGGCCC CGACCAGTCA     2700

GCGCCTGGCC CGCTACGTGC GCCCCGACGA GCTGCACCAG GCGTTCAACA TGGCGCTGCT     2760

GGAGTCGCCC TGGTCGGCCG ACGGCTTCCG CGCGGTCATC GACGACTCGC TCGCGGCCAA     2820

CGACGCCGTC GGGGCCACCA CGACCTGGGT GCTGGGCAAC CACGACGTCA AGCGCCCGGT     2880

GACCCGCTAC GGCGACGGCG CCACCGGCCT GCGCCGGGCG CGGGCGGCGG CGCTGCTCAG     2940
```

-continued

```
CTTCGCGCTG CCGGGCTCGG TCTACGTCTA CCAGGGGGAG GAGCTGGGGC TGCCGGAGGT   3000

GCTGGACCTG CCGGAGGAGG TGCTGCAGGA CCCGGTGTGG GAGCGCTCCG GGCGCACAGA   3060

CCGGGGCCGC GACGGCTGCC GCGTGCCGAT GCCGTGGGAG GGTGCCGACG CGCCGTTCGG   3120

GTTCGGTCCG GCCGGGAGCT GGCTGCCCGT CCCGCCCGGC TGGGCGCAGC TGTCGGTCGA   3180

GGCCCAGCGC GAGCGCGACG ACTCGGTGCT GTCGACCTAC CGCAAGGCGC TCGCGCTGCG   3240

GCGAGAGCTC GGCTCGGACG TCTGGAGTG GATGGATGCC CCCTCGGGCG TCCTTGCCTT   3300

CCGGCGCGGT CCCGGACTGG TGTGCGCGGT GAACTTCGGT TCCGAACCGG TGTCGCTGGA   3360

CCTGCCGGGA CGGCTGCTGT GCCGCAGCGA CGCGGGCGCC GACTGGTCGG TGTGCTACC   3420

GGGCGACACC GCCGTCTGGC TGGCGGGCTG AGCGGGAGGC CCGGCGGGGA AGGATTCACC   3480

GAGAATCCTC CCAATAGGTC TATTTCTTGC CGGACCGGCG TGGTCACATC GATACCCCCT   3540

GCACACGAGG AGGTAGTCGA TGACCATCTT GCGGCGATTA GCCGTCGGCG CCGCGGCACT   3600

GGCGCTCGCG GGGTTGGGCG TGGTCGGCAT CGGGCAGACG CCCGCGTCGG CCGCGCCCAA   3660

CTTCCAGGTG CCCTTCGCCT GCGGTGTCAC CGTCACCGCG GCCACGTTCA GCGGCCACAA   3720

CCCGCCCAAC TCGGTCGACT TCCAGAAGAG CGGCATCACC GGCATGCCGG TGCTCGCATC   3780

CGCCGCGGGC AAGATCACCA GGGTGGCCAA CGAGGGCGAC ACCAGCTACG GCGATGGGT   3840

CGAGATCGAC CACGGTGCCG GCTGGACCAC CCGCTACGCG CACCTGAACA GCCAGACCGT   3900

CTCGGTCGGC CAGCAGGTCG CGCTCGGCGC AAGATCGGC ACCGCCGGTG CGACCGGCGG   3960

CGTGACCGGG CCCCACCTGC ACTACGAACA GCGCCTCAAC GGCACCGCGC AGAAGGCCAA   4020

GCTCAACGGC GTCGCGGTCC CGTACTACGG CCACACCGAC TTCACCAGCA AGAACAACTG   4080

CAGCGGCAAC CCCTACACGC CGACCGAGGT GTGCGGCGCC GGCTACAGCG TGATCGACCA   4140

GCAGGCGCTG GGCGGCGCGG GCACCACCTA CCTGCTCTAC AACGCGTCCA ACGCCGGCAA   4200

CTGCGTGGTC ACGCTGAAGG CCAGGTCGCT GGGCACCGCG ACGGCGACCT CGGCGTTCCT   4260

GGAGGTCGAG GGGACCGCGC GGGTCACCGA CAGCGGCAAC TTCACCTACT ACGCGGGCCC   4320

GGTGCGCAAG GTCGCCGAGG CCACCTGCGT GAAGTGGGGC GGCTCGGTCG GTTCGGAGTC   4380

CTACACCAGC CCGTTCGAGC ACTGCGGCTA GGCAGAACCT CGTTGCTGTC CTTGAACTCG   4440

CCTTGCGTGG CGGTTCCGGT GGCGGAACCT CAGGCGTCCT CTGGCTCCGG GACCTTTTTC   4500

TGACGTATGC CCATACGCTG CGAAAAAGCT GTCCTCGCCA GAGGACGCCT GAGAACCCGC   4560

GGCGGTGCGG GTTGCGGGGT GGGCCAAGCG GCTGCGCCGC TTCAAAGACC TGCTAGAAGA   4620

CGGACCAGCC GGTCAGCGTG GTGAAGTGGT CGAGGGCGGC AACGCCCGCC ACCGAGTTGC   4680

CGCGCCGGTC CAGGCCGGGG CTCCACACCG CGACCGCGCA GCGGCCCGGC ACGATCGCCA   4740

GGATGCCGCC GCCGACGCCG CTCTTGCCCG GGATCC                              4776
```

(2) INFORMATION FOR SEQ ID NO:2:

(i) SEQUENCE CHARACTERISTICS:
        (A) LENGTH: 341 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:2:

```
Val Ala Gly Leu Ser Asp Ile Ala Lys Ala Ala Gly Val Ser Val Ser
1               5                   10                  15

Thr Val Ser Arg Val Leu Met Arg Arg Ala Gly Ile Lys Glu Asp Thr
```

```
            20                  25                  30
Arg Gln Arg Val Leu Ala Val Leu Asn Glu Met Pro His Thr Ala Arg
        35                  40                  45
Gly Ile Gly Ala Leu Arg Arg Thr Gly Val Ile Gly Leu Leu Val Pro
        50                  55                  60
Glu Leu Ser Asn Pro Val Phe Pro Ala Phe Glu Ala Leu Glu Ala
65                  70                  75                  80
Arg Ala Val Gly Ala Gly Tyr Ala Ser Leu Leu Cys Asn Thr Arg Val
                85                  90                  95
Gly Met Ser Glu Glu Asp Tyr Val Arg Met Leu Ile Ala Arg Gly Val
                100                 105                 110
Glu Gly Met Val Phe Val Ser Pro Glu Ile Ala Asn Thr Glu Gly Glu
                115                 120                 125
Gln Arg Ile Ser Arg Ser Tyr Tyr Glu Lys Leu Leu Ala Asp Gly Val
                130                 135                 140
Arg Met Val Phe Val Asn Gly Gly Ala Pro Thr Leu Asp Val Pro Asp
145                 150                 155                 160
Val Ala Val Asp Glu His Leu Ala Gly Tyr Thr Ala Thr Arg His Leu
                165                 170                 175
Leu Asp Leu Gly His Arg Arg Ile Gly Phe Val Ser Gly Pro Ala Arg
                180                 185                 190
Ala Val Pro Ser Arg Leu Lys Arg Ala Gly Trp Ala Ala Ala Leu Glu
                195                 200                 205
Glu Ala Asp Ile Ala Pro Asp Pro Arg Leu Val Ala His Ala Pro Phe
                210                 215                 220
Gly Ala Glu Gly Gly Ala Gln Ala Met Ala Glu Leu Leu Glu Thr Ala
225                 230                 235                 240
Gly Pro Thr Ala Val Met Cys Ser Ser Asp Val Met Ala Leu Gly Ala
                245                 250                 255
Met Arg Glu Ala Lys Arg Arg Gly Leu Ala Thr Pro Glu Asp Leu Ser
                260                 265                 270
Val Val Gly Phe Asp Asp Ile Ala Leu Ala Ser Tyr Cys Gln Pro Ala
                275                 280                 285
Leu Thr Thr Leu Ala Gln Pro Ile Glu Glu Met Ala Ala Ala Ala Val
    290                 295                 300
Asp Glu Leu Ser Arg Arg Leu Asp Pro Asp Gln Pro Gly Arg Ala Thr
305                 310                 315                 320
Thr Ser Phe Ser Arg Met Phe Arg Pro Asn Leu Val Val Arg Glu Ser
                325                 330                 335
Thr Ala Ala Pro Arg
            340

(2) INFORMATION FOR SEQ ID NO:3:

(i) SEQUENCE CHARACTERISTICS:
        (A) LENGTH: 526 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

Val Leu Arg Gly Ala Gly Val Arg Gly Thr Ala Ala Asp Trp Trp Arg
1               5                   10                  15

Asp Ala Val Val Tyr Gln Val Tyr Val Arg Ser Phe Ala Asp Ala Asp
                20                  25                  30
```

```
Gly Asp Gly Ile Gly Asp Leu Ala Gly Val Arg Ala Arg Leu Pro Tyr
        35                  40                  45
Leu Val Glu Leu Gly Val Asp Ala Val Trp Leu Thr Pro Phe Tyr Pro
    50                  55                  60
Ser Pro Met Ala Asp Gly Gly Tyr Asp Val Ala Asp Tyr Cys Asp Val
65                  70                  75                  80
Asp Pro Met Phe Gly Thr Leu Asp Phe Asp Asp Leu Leu Ala Arg
                85                  90                  95
Ala His Ser Leu Gly Leu Lys Val Ile Val Asp Val Val Pro Asn His
            100                 105                 110
Thr Ser Asp Ala His Pro Trp Phe Ala Glu Ala Leu Glu Ala Gly Pro
        115                 120                 125
Gly Asp Pro Ala Arg Glu Arg Tyr Leu Phe Arg Asp Gly Arg Gly Glu
    130                 135                 140
Ser Gly Glu Leu Pro Pro Asn Asp Trp Glu Ser Ser Phe Gly Gly Pro
145                 150                 155                 160
Ala Trp Thr Arg Val Pro Asp Gly Gln Trp Tyr Leu His Leu Phe Ala
                165                 170                 175
Pro Glu Gln Pro Asp Leu Asn Trp Arg Asn Pro Gln Ile Arg Ala Glu
            180                 185                 190
Phe Ala Lys Val Leu Glu Phe Trp Leu Asp Arg Gly Val Asp Gly Phe
        195                 200                 205
Arg Ile Asp Val Ala His Gly Met Ile Lys His Pro Asp Leu Pro Asp
    210                 215                 220
Thr Gly Leu His Gln Gln Ile Ser Leu Leu Gly Arg Ala Glu Leu Pro
225                 230                 235                 240
Tyr Phe Asp Gln Asp Glu Val His Gly Ile Tyr Arg Glu Trp Arg Glu
                245                 250                 255
Leu Leu Asp Ser Tyr Glu Gly Ala Arg Ile Gly Val Ala Glu Ala Trp
            260                 265                 270
Ala Pro Thr Ser Gln Arg Leu Ala Arg Tyr Val Arg Pro Asp Glu Leu
        275                 280                 285
His Gln Ala Phe Asn Met Ala Leu Leu Glu Ser Pro Trp Ser Ala Asp
    290                 295                 300
Gly Phe Arg Arg Val Ile Asp Asp Ser Leu Ala Asn Asp Ala Val
305                 310                 315                 320
Gly Ala Thr Thr Thr Trp Val Leu Gly Asn His Asp Val Lys Arg Pro
                325                 330                 335
Val Thr Arg Tyr Gly Asp Gly Ala Thr Gly Leu Arg Arg Ala Arg Ala
            340                 345                 350
Ala Ala Leu Leu Ser Phe Ala Leu Pro Gly Ser Val Tyr Val Tyr Gln
        355                 360                 365
Gly Glu Glu Leu Gly Leu Pro Glu Val Leu Asp Leu Pro Glu Glu Val
    370                 375                 380
Leu Gln Asp Pro Val Trp Glu Arg Ser Gly Arg Thr Asp Arg Gly Arg
385                 390                 395                 400
Asp Gly Cys Arg Val Pro Met Pro Trp Glu Gly Ala Asp Ala Pro Phe
                405                 410                 415
Gly Phe Gly Pro Ala Gly Ser Trp Leu Pro Val Pro Pro Gly Trp Ala
            420                 425                 430
Gln Leu Ser Val Glu Ala Gln Arg Glu Arg Asp Asp Ser Val Leu Ser
        435                 440                 445
Thr Tyr Arg Lys Ala Leu Ala Leu Arg Arg Glu Leu Gly Ser Asp Gly
```

```
                       450             455             460
Leu Glu Trp Met Asp Ala Pro Ser Gly Val Leu Ala Phe Arg Arg Gly
465                 470             475                 480

Pro Gly Leu Val Cys Ala Val Asn Phe Gly Ser Glu Pro Val Ser Leu
                485             490                 495

Asp Leu Pro Gly Arg Leu Leu Cys Arg Ser Asp Ala Gly Ala Asp Trp
            500             505             510

Ser Gly Val Leu Pro Gly Asp Thr Ala Val Trp Leu Ala Gly
            515             520             525

(2) INFORMATION FOR SEQ ID NO:4:

(i) SEQUENCE CHARACTERISTICS:
        (A) LENGTH: 283 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Met Thr Ile Leu Arg Arg Leu Ala Val Gly Ala Ala Leu Ala Leu
1               5                   10                  15

Ala Gly Leu Gly Val Val Gly Ile Gly Gln Thr Pro Ala Ser Ala Ala
                20              25              30

Pro Asn Phe Gln Val Pro Phe Ala Cys Gly Val Thr Val Thr Ala Ala
            35              40              45

Thr Phe Ser Gly His Asn Pro Pro Asn Ser Val Asp Phe Gln Lys Ser
        50              55              60

Gly Ile Thr Gly Met Pro Val Leu Ala Ser Ala Ala Gly Lys Ile Thr
65              70              75                  80

Arg Val Ala Asn Glu Gly Asp Thr Ser Tyr Gly Arg Trp Val Glu Ile
                85              90                  95

Asp His Gly Ala Gly Trp Thr Thr Arg Tyr Ala His Leu Asn Ser Gln
            100             105             110

Thr Val Ser Val Gly Gln Gln Val Ala Leu Gly Ala Lys Ile Gly Thr
        115             120             125

Ala Gly Ala Thr Gly Gly Val Thr Gly Pro His Leu His Tyr Glu Gln
130             135             140

Arg Leu Asn Gly Thr Ala Gln Lys Ala Lys Leu Asn Gly Val Ala Val
145             150             155             160

Pro Tyr Tyr Gly His Thr Asp Phe Thr Ser Lys Asn Asn Cys Ser Gly
                165             170             175

Asn Pro Tyr Thr Pro Thr Glu Val Cys Gly Ala Gly Tyr Ser Val Ile
            180             185             190

Asp Gln Gln Ala Leu Gly Gly Ala Gly Thr Thr Tyr Leu Leu Tyr Asn
        195             200             205

Ala Ser Asn Ala Gly Asn Cys Val Val Thr Leu Lys Ala Arg Ser Leu
210             215             220

Gly Thr Ala Thr Ala Thr Ser Ala Phe Leu Glu Val Glu Gly Thr Ala
225             230             235             240

Arg Val Thr Asp Ser Gly Asn Phe Thr Tyr Tyr Ala Gly Pro Val Arg
                245             250             255

Lys Val Ala Glu Ala Thr Cys Val Lys Trp Gly Gly Ser Val Gly Ser
            260             265             270

Glu Ser Tyr Thr Ser Pro Phe Glu His Cys Gly
        275             280
```

(2) INFORMATION FOR SEQ ID NO:5:

(i) SEQUENCE CHARACTERISTICS:
        (A) LENGTH: 53 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Phe Val Ser Trp Gly Thr Leu Thr Thr Phe His Asp Leu Ala Ala Val
1               5                   10                  15

Gly Ala Val Ser Asn Gly Arg Arg Asp Leu Gly Pro Ser Trp Val Ala
            20                  25                  30

Val Ala Cys Arg Gly Pro Val Ile Ala Leu Ile Gly Gly Gly Val Gly
            35                  40                  45

Ser Lys Gly Pro Ile
50
```